(12) United States Patent
Silver et al.

(10) Patent No.: US 6,778,630 B2
(45) Date of Patent: Aug. 17, 2004

(54) METHOD AND SYSTEM FOR RECONSTRUCTING COMPUTED TOMOGRAPHY IMAGES USING REDUNDANT DATA

(75) Inventors: Michael D. Silver, Northbrook, IL (US); Katsuyuki Taguchi, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/103,781

(22) Filed: Mar. 25, 2002

(65) Prior Publication Data

US 2003/0123614 A1 Jul. 3, 2003

(30) Foreign Application Priority Data

Mar. 23, 2001 (JP) .................................. P2001-084988

(51) Int. Cl.[7] .................................................. A61B 6/03
(52) U.S. Cl. ............................. 378/15; 378/4; 378/901
(58) Field of Search ........................... 378/4, 8, 15, 19, 378/901

(56) References Cited

U.S. PATENT DOCUMENTS 5,270,923 A     12/1993  King et al.
5,805,659 A     9/1998   Tam ............................. 378/15
6,185,271 B1    2/2001   Kinsinger ..................... 378/19
6,201,849 B1 *  3/2001   Lai ............................... 378/4
6,452,996 B1 *  9/2002   Hsieh ........................... 378/15
6,542,570 B1 *  4/2003   Silver ........................... 378/4

FOREIGN PATENT DOCUMENTS

JP     2001-299738     10/2001

OTHER PUBLICATIONS

Michael D. Silver;; "A Method For Including Redundant Data in Computed Tomography"; Medical Physics; Apr. 2000, pp. 773–774.

* cited by examiner

Primary Examiner—David V. Bruce
(74) Attorney, Agent, or Firm—Oblon, Spivak, McClelland, Maier & Neustadt, P.C.

(57) ABSTRACT

A method and system for reconstructing an x-ray image from a partial orbit through the use of a "virtual" fan angle. The virtual fan angle is determined based upon the range of angular positions spanned by a source in a CT instrument or a selected smaller angle. Exposure data is obtained and he virtual fan angle is used to weight the exposure data. Image reconstruction can then proceed using the weighted exposure data. The described methods and system also function for data collected over a complete orbit.

24 Claims, 23 Drawing Sheets

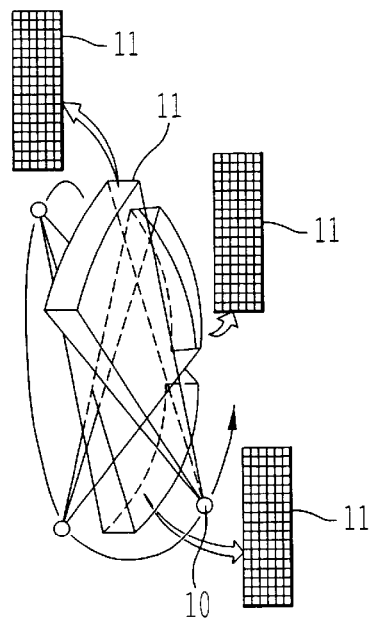
FIG. 18
FIG. 19
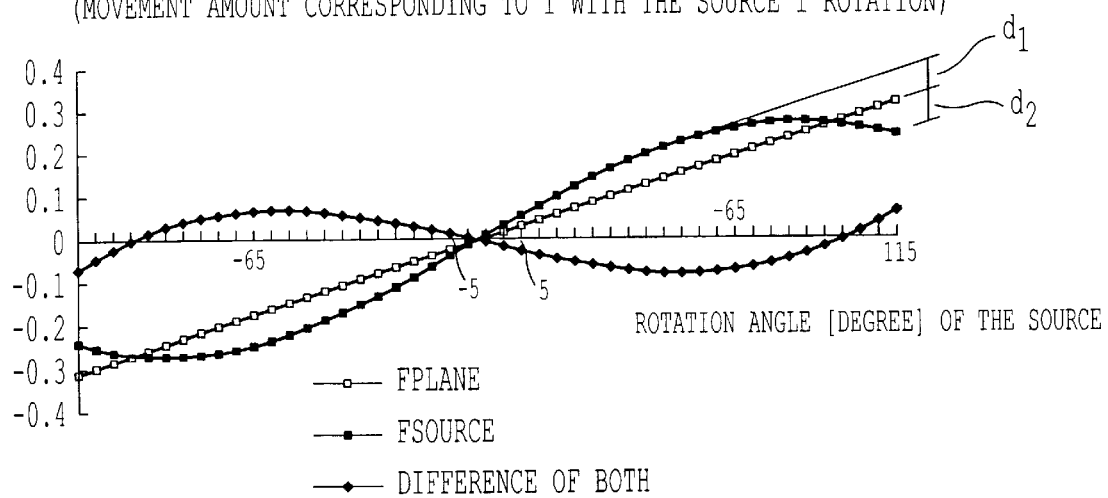

[(RECONSTRUCTED SURFACE) OF IMAGINARY SURFACE DURING ROTATION, P(5)]
[ILLEGIBLE FORMULA]

WHEN RECONSTRUCTION IS AT THE SAME TIME AS COLLECTION,
AT THE TIME OF 1=DELTA L, COLLECTION IS COMPLETE AFTER RECONSTRUCTION ns from Japanese
METHOD AND SYSTEM FOR RECONSTRUCTING COMPUTED TOMOGRAPHY IMAGES USING REDUNDANT DATA

CROSS-REFERENCE TO RELATED APPLICATIONS

The present application claims priority from Japanese Application JP2001-084988, the contents of which are herein incorporated by reference.

BACKGROUND OF THE INVENTION

1. Field of the Invention

The present invention relates to a method and system for image reconstruction in fan- or cone-beam X-ray computed tomography and, in particular, to a method and system for reconstructing images using weighting coefficients to weight exposure data.

2. Discussion of the Background

Fan- and cone-beam computed tomography (CT) reconstructs the interior of an object of interest or patient from one-dimensional and two-dimensional projections, respectively, of transmitted x-rays through the object of interest or patient. An x-ray source and an x-ray detector are arranged in a number of different positions so that x-rays transmitted through the object of interest are received at the detector. The detector, either alone or in conjunction with other devices, generates image data for each position of the source and/or detector. The image data is then stored, manipulated, and/or analyzed to reconstruct the interior of the object. In a fan-beam system, the detector forms a linear array of x-ray sensing elements while in a cone-beam system, the detector forms an array of x-ray sensing elements.

The classical path of the x-ray source and detector is along a complete circular orbit, i.e. 360°, about the object of interest. The source and detector are mechanically joined so as to maintain a constant separation distance and position relative to each other and then revolved around the object.

As shown in FIG. 1, an X-ray source S emits either a cone- or a fan-beam of X-rays toward a detector D. The X-rays emitted by source S are incident upon a three-dimensional object of interest (not shown) such as a calibration phantom, a patient, a test object, or other article of interest. At least a portion of the X-rays generated at point source S pass through or around the object and are received at the detector D. The source S and the detector D are fixed relative to one another and revolve in a substantially circular orbit about an axis A in, for example, a C-arm gantry or ring gantry device. The angular position of the X-ray source S is illustrated here as the angle $\beta$ relative to an arbitrary half-line L that terminates at the rotation axis A.

Several disadvantages of complete circular orbits of the source and detector about the object arise due to the nature of the complete orbit itself. Electrical leads must be capable of circumscribing one or more complete revolutions about the object of interest. In medical CT, since the patient must be contained within the orbiting detector and source, access to the patient by medical personnel is hindered. Furthermore, many patients dislike being enclosed within the CT mechanism for the extended times necessary to gather sufficient image data for meaningful reconstruction.

In fan-beam CT, the detector D is a substantially linear array of detector elements typically in arc form on the array source. In cone-beam CT, detector D is an area array of detector elements. Curved line and curved surface arrays of detector elements are also suitable for use as detector element D. In all of these cases, detector element D will have a cross sectional area with a width W in a plane orthogonal to the axis of rotation A. In this particular embodiment, the midpoint of the width of a linear array detector D is substantially positioned at a line N passing through the center of the source S and the axis A.

The angle $\gamma$ illustrated in FIG. 1 describes the angle of a ray O joining the source S and one element selected from the matrix of elements that constitutes the detector D. In fan-beam CT, the angle $\gamma_m$ describes the rays M with the largest (maximum) angle relative to the line N, where the ray M is emitted by the source S and received by the detector D. The physical limit on ray M and hence angle $\gamma_m$ can arise due to, for example, the finite length of the detector D (as illustrated), collimation of the source emission (not shown), or the non-omnidirectional emission of X-rays by the source S (also not shown). In FIG. 1 with the midpoint of the cross-sectional area of detector D located at line N, the angle $\gamma_m$ on one side of the axis is equal and opposite to angle $\gamma_m$ on the other side of the axis. Shifting the detector D relative to line N will change this relationship between the two $\gamma_m$'s and can be accounted for using traditional geometric rules.

FIGS. 2a–c illustrate three example rays $O_a$, $O_b$, and $O_c$ over which the same x-ray transmittance is measured at two different angular positions of the source $\beta$ relative to an arbitrary half-line L and fan beam angles $\gamma$. For illustrative purposes, the first angular positions of the source $\beta$ is equal to zero in all three examples. In FIG. 2a, ray $O_a$ is the first ray sampled twice, while FIGS. 2b and 2c show respective rays $O_b$ and $O_c$ that are sampled twice at other positions.

In recent years, there has been an attempt to implement fan- and cone-beam CT on gantries that only revolve around a portion of the object or patient during imaging. Such partial orbits are capable of providing complete image data for reconstruction of the interior of an object since many views in a complete circular orbit are redundant, i.e., the image data provide little or no new information. For example, if the object of interest is immobile and the system is ideal (i.e., no noise), switching the location of the source and detector will provide no new information along the ray through the axis even though image data from a second view has been collected.

The advantages of such partial orbits include easier and less expensive mechanical realization, providing access to a patient during medical imaging and enabling supporting mechanisms for the source and detector that do not require complete enclosure of the patient. Also, it allows the use of x-ray imaging and primarily designed for non-CT imaging application to also be used to obtain a CT-image for special needs.

A method for reconstruction of one particular partial orbit, namely an orbit that covers the "minimal complete data set" has been described by Dennis Parker ("Optimal Short Scan Convolution Reconstruction for Fanbeam CT," Med. Phys. 9, 254–257, 1982) which is incorporated herein by reference. The "minimal complete data set" is the collection of equally-spaced projection image data that can be used in conventional, convolution type, reconstruction methods. The "minimal complete data set" spans more than one half of a complete orbit. Namely, it spans 180° plus the maximum fan angle $2\gamma_m$, where the maximum channel angle $\gamma_m$ is the largest angle of a ray emitted by the X-ray source that is received at the (substantially two- or three-dimensional)

X-ray detector relative to the ray emitted from the source that passes through the axis of rotation of the X-ray source and detector. FIG. 1 schematically illustrates this and other terminology used to describe the current invention.

One disadvantage with the use of such a "minimal complete data set" orbit lies in the fact that certain rays are sampled twice as often as other rays. In other words, certain image data is collected twice as often as other image data and are redundant. Illustrative examples are illustrated diagrammatically in FIGS. 2a–c. This can be better illustrated in FIG. 3, where the image data is represented in Radon space. The horizontal axis in FIG. 3 corresponds to the channel angle $\gamma$, the vertical axis corresponds to the angular position $\beta$ of the x-ray source, and, in an actual Radon space representation of a collection of x-ray image data, the grey level of each point in Radon space would correspond to the line integral of the x-ray transmittance along the particular ray defined by the fan angle $\gamma$ and the angular position of the source $\beta$. FIG. 3 indicates the angular positions of the source and the channel angles for rays that are sampled shown by shaded regions during the collection of a "minimal complete data set" partial orbit (including those rays illustrated in FIGS. 2a–2c). Such Radon space representations of image data are well-known in the art, and a more complete explanation of these representations can be found in several textbooks including "Image Reconstruction From Projections: The Fundamentals of Computerized Tomography" by Gabor T. Herman, Academic Press, New York, 1980, p. 36–39 and 161–165, the entire contents of which is incorporated herein by reference. In general, the line integrals along the rays $p(\beta,\gamma)$ and $p(\pi+\beta+2\gamma,-\gamma)$ are equivalent. When the total collection of image data is used to reconstruct the interior of an object, the twice collected image data distorts the appearance of the final image and yields poor quality images.

Various methods and devices for solving this problem with the minimal complete data set have been proposed and implemented. The image data can be rebinned into parallel ray data sets and then analyzed, but this requires further computational effort and time. Naparstek described several alternate methods (IEEE Trans. Nucl. Sci. NS-27, p. 1112 ff., 1980, which is hereby incorporated by reference) that, however, provided inadequate results.

Parker has described a method for solving the problem of oversampling certain ray lines during minimal data reconstruction in fan-beam computed tomography with the divergent beam geometry by introducing weights for the oversampled image data. These weights are required to satisfy Equation (1), namely that $$w(\beta,\gamma)+w(\pi+\beta+2\gamma,-\gamma)=1 \quad (1)$$

Parker or Crawford and King ("Computed Tomography Scanning with Simultaneous Patient Translation" Med. Phys. 17, 967–982, 1990 and incorporated herein by reference) give explicit formulae for the weights.

Unfortunately, simple and elegant methods and devices for reconstruction using partial orbits intermediate to the minimal complete data set and the complete orbit have yet to be developed.

SUMMARY OF THE INVENTION

It is an object of the invention to increase the helical pitch in cone-beam scanning.

It is another object of the invention to use a helical pitch determined using the field of view in a scanner.

These objects can be realized by an image reconstruction method and system that uses a "virtual" fan angle that is equal to the angular rotation about the axis beyond 180° (regardless of the actual fan angle). Alternatively, the "virtual" fan angle is defined as a selected angle that is less than the angular rotation about the axis beyond 180°, but still larger than the angle for collection of the minimal complete data set. The only constraint on the virtual fan angle in both cases is that it is larger than the physical fan angle of the instrument or, in other words, the exposure path is intermediate to the minimal complete data set and a 360° path. The virtual fan angle can be used to calculate weights for the oversampled rays that are used during reconstruction of the interior of objects.

Specifically, a system using such a virtual fan angle will include an X-ray tomograph configured to produce an exposure path of a source about an object of interest that is less than 360° but greater than 180° plus the fan angle. The virtual fan angle can be determined using either the actual angle spanned by such an orbit or a selected smaller angle still larger than the angle necessary to collect the minimal complete data set, and will be used to determine non-uniform weights for the data collected from rays through the orbit and/or to identify the rays to which such weights will be applied. The weighted data can then be used to reconstruct an image according to any of a number of different reconstruction methods.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 18 is a conceptual diagram illustrating changes in a group of intersection points on the detection plane of approximate paths with respect to changes in rotation angles;

FIG. 19 is a diagram illustrating the device for the helical trajectory of the X-ray source and the virtual plane unit;

DETAILED DESCRIPTION OF THE PREFERRED EMBODIMENTS

Figure 5:
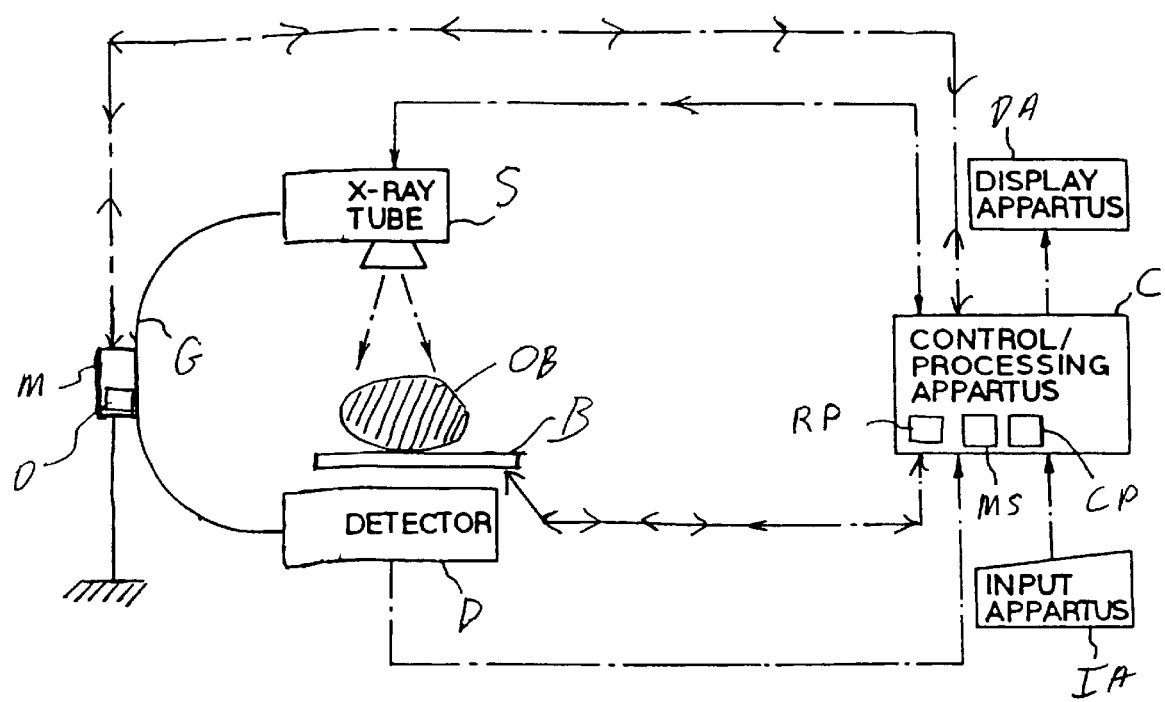
FIG. 5 is a diagram of a C-arm gantry device according one embodiment of the invention.
Figure 6:
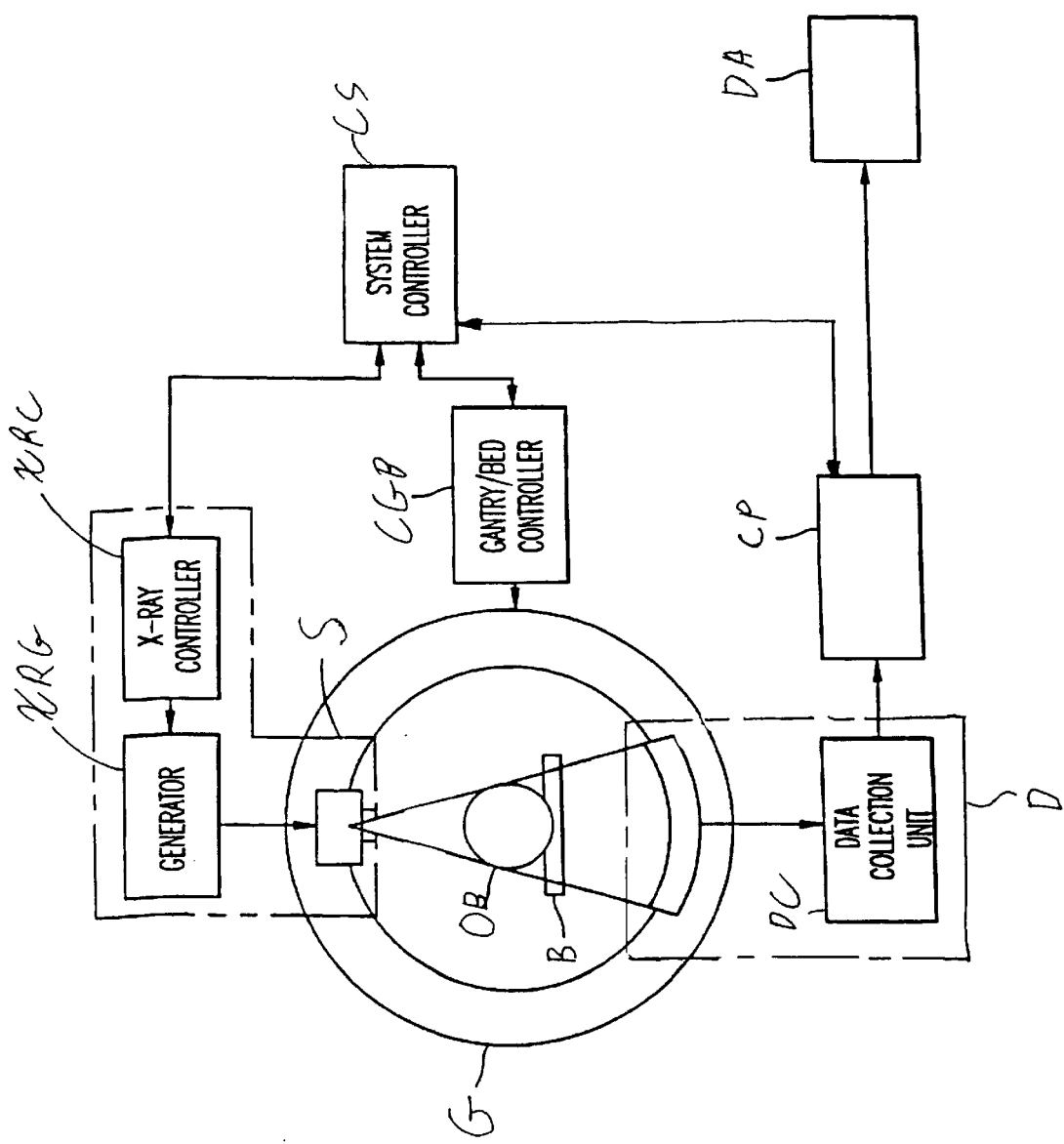
FIG. 6 is a diagram of a helical cone-beam device according to another embodiment of the invention.

Referring now to the drawings, wherein like reference numbers designate identical or corresponding parts throughout the several views, and more particularly to FIGS. 5 and 6 thereof, which illustrate systems for performing CT imaging according to embodiments of the invention, namely a C-arm gantry and a fan-beam or cone-beam CT system, respectively.

In the present invention a "virtual" fan angle may be set up that does not depend on an actual physical maximum fan angle. The "virtual" fan angle can be set as an arbitrary angle which is different from the physical maximum fan angle. The weighting function of an oversampled certain ray lines for reconstructing an image can be calculated by using the virtual fan angle. In detail, the image reconstruction can be achieved from data of a scanning range (projection data span) which is larger or smaller than 180 degrees plus the maximum fan angle and is less than 360 degrees and more than 180 degrees. By setting up a fan angle virtually, the virtual fan angle is simply applied to the weighting function determination method employed in the conventional half-scanning method, and the weighting function is easily determined. Therefore, an uneven weighting function for the projection data can be given suitably and simply. The weighted data can be used for reconstructing the images according to one of various methods.

Figure 1:
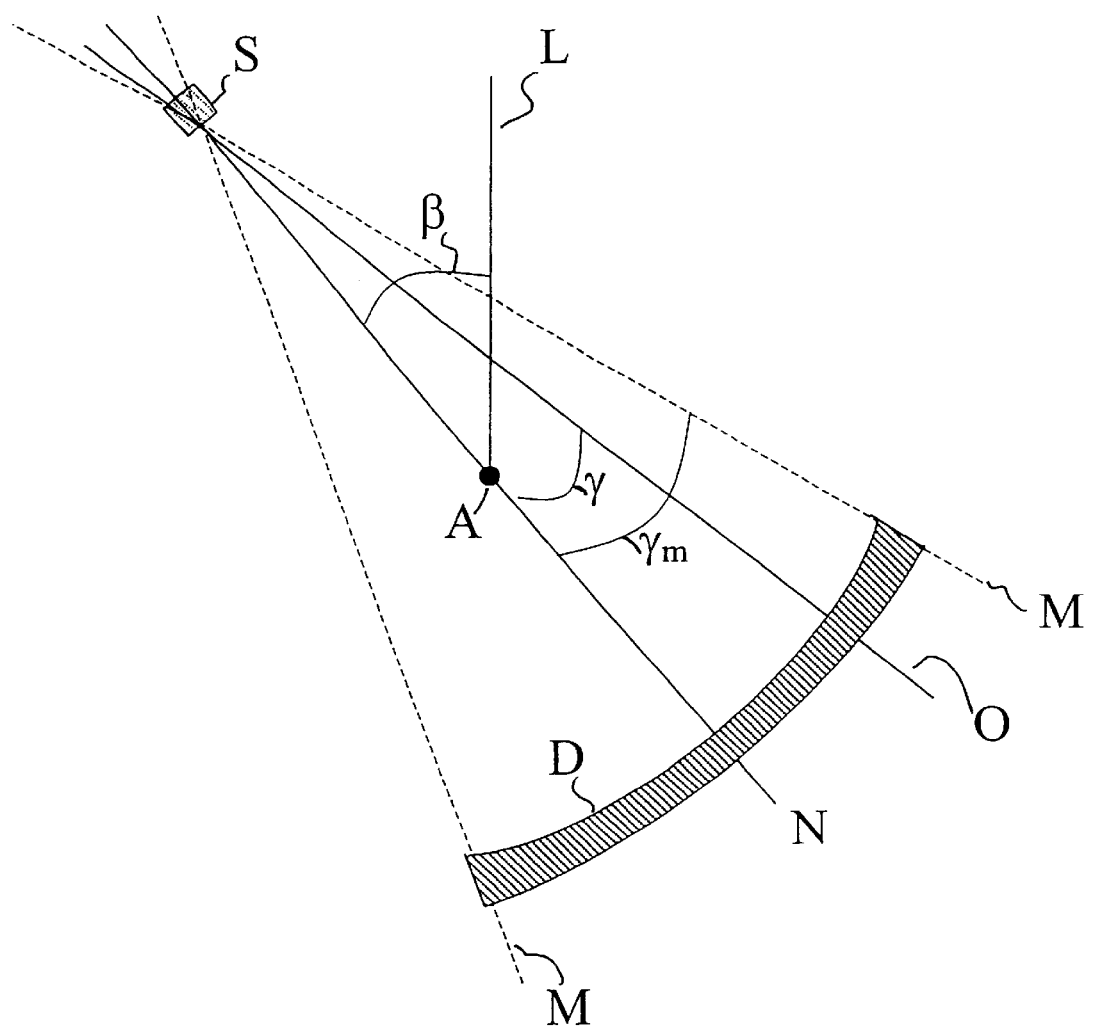
FIG. 1 is a diagram illustrating the coordinate system used to describe the current invention.

A first embodiment of the system according to the invention using fan-beam CT on a diagnostic CT-gantry is shown in FIG. 6. The coordinate system used to describe the current invention is shown in FIG. 1. The projection data measurement system accommodates an X-ray source S that generates a substantially fan-shaped beam of X-ray flux and a linear array X-ray detector D consisting of a linear array of detector elements. X-ray source S and detector D are installed with faces opposing one another on a rotating ring gantry G. An object or patient OB can be placed within the ring gantry G upon a slidably supported bed B. When X-rays generated at source S (or a portion thereof) pass through object OB and are incident upon detector D, detector D transducers the intensity of these X-rays, and the electrical signal is provided to the control/processing apparatus CP after amplification and/or encoding by a data collection unit DC included in detector D. In contrast with FIG. 5, the embodiment of FIG. 6 is provided with a system controller CS external to the control/processing apparatus CP. This system control is responsible for controlling the translation of bed B and movement of gantry G using gantry/bed controller CGB, the firing of source S (in conjunction with X-ray controller XRC and X-ray generator XRG), and the rotation of either bed B about the axis of ring gantry G or the revolution of source S and detector D along an orbit defined by ring gantry G. Data is collected, stored, and manipulated (including weighting and reconstruction) by control/processing apparatus CP. Data from CP can be displayed upon display apparatus DA.

Figure 2A:
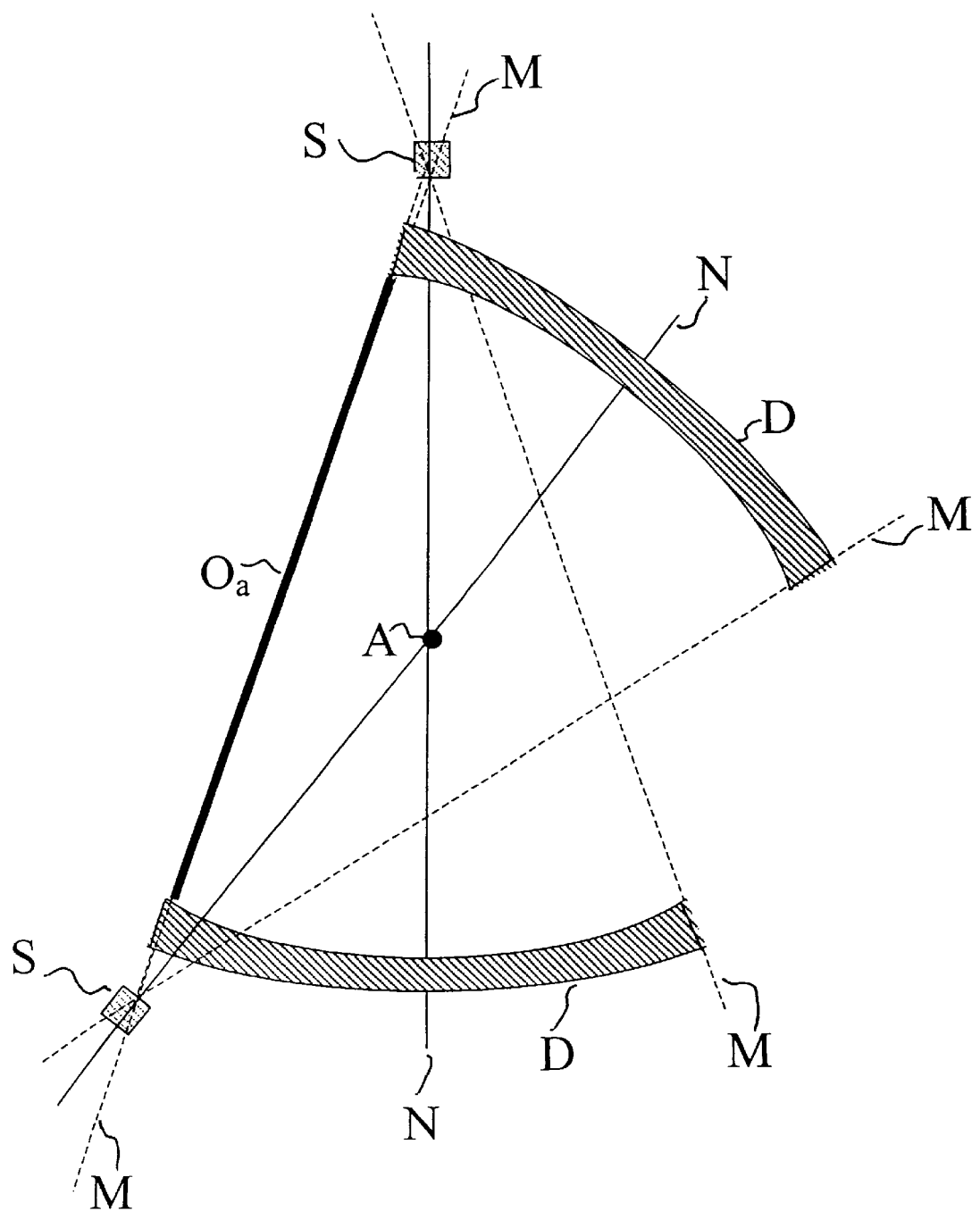
FIGS. 2a–c are diagrammatic illustrations of example rays at various angular positions of the source $\beta$ that are sampled twice along an orbit that spans an angle equal to or larger than the angle spanned for the collection of a "minimal complete data set" partial orbit.
Figure 2B:
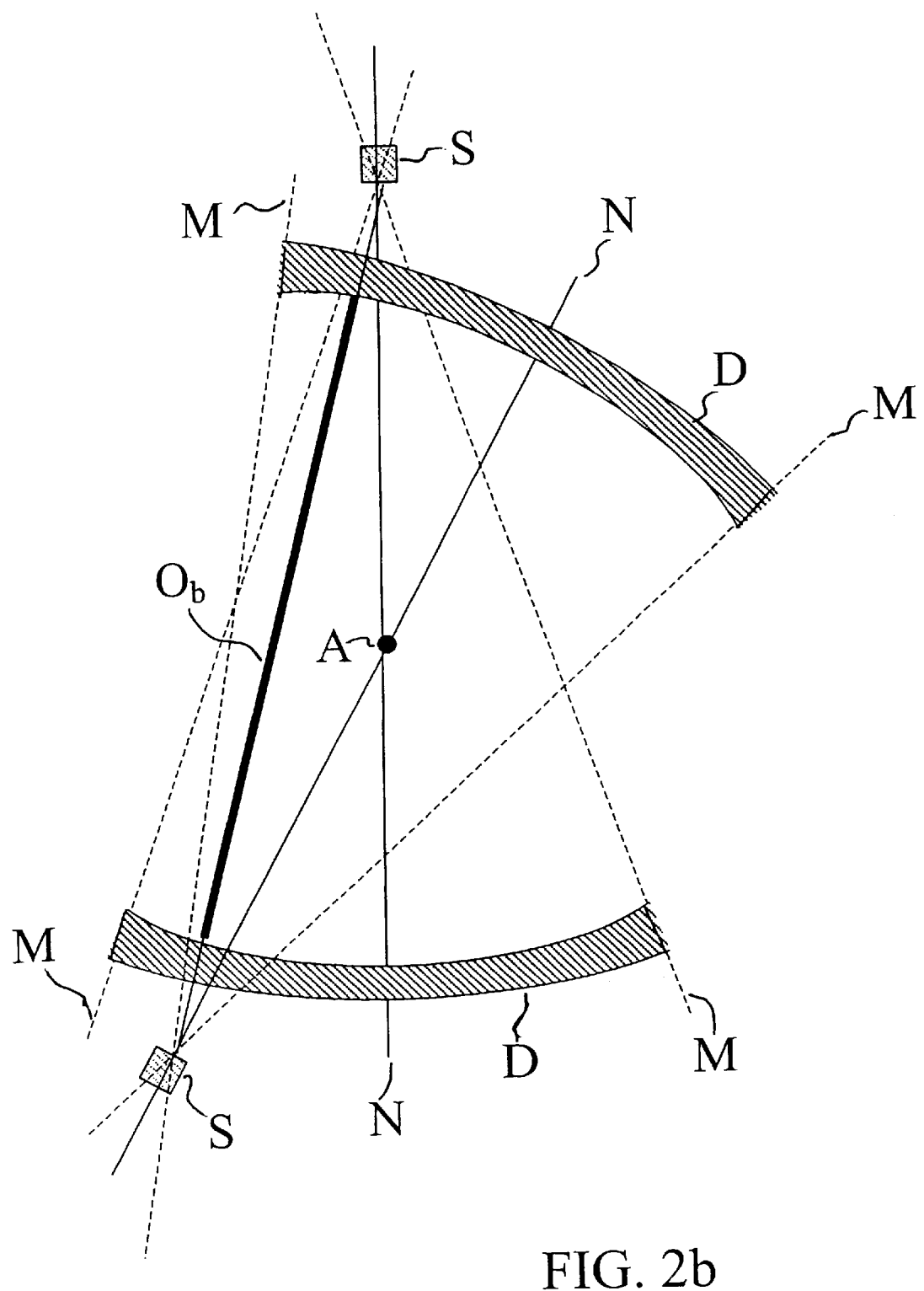
Figure 2C:
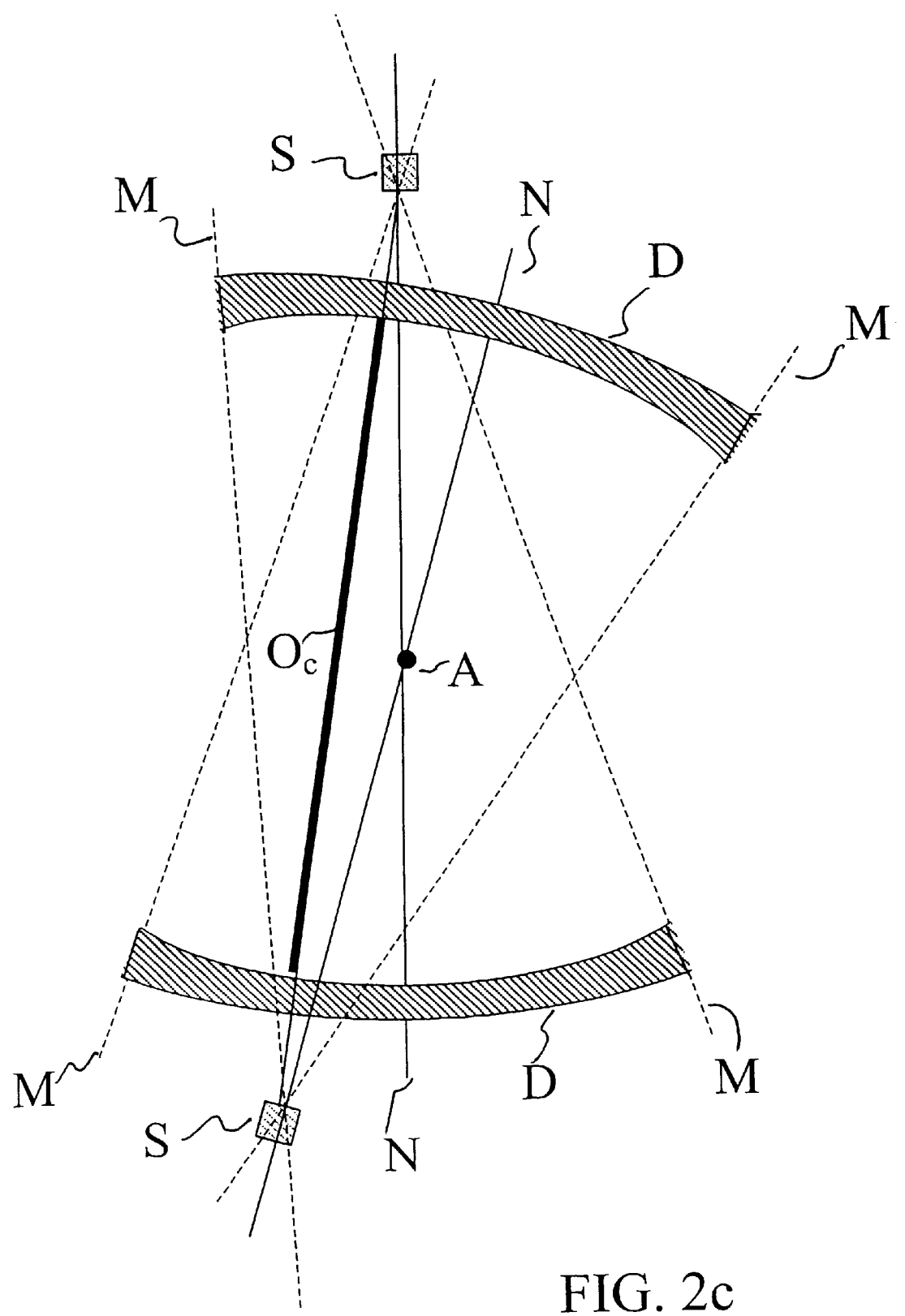
Figure 2D:
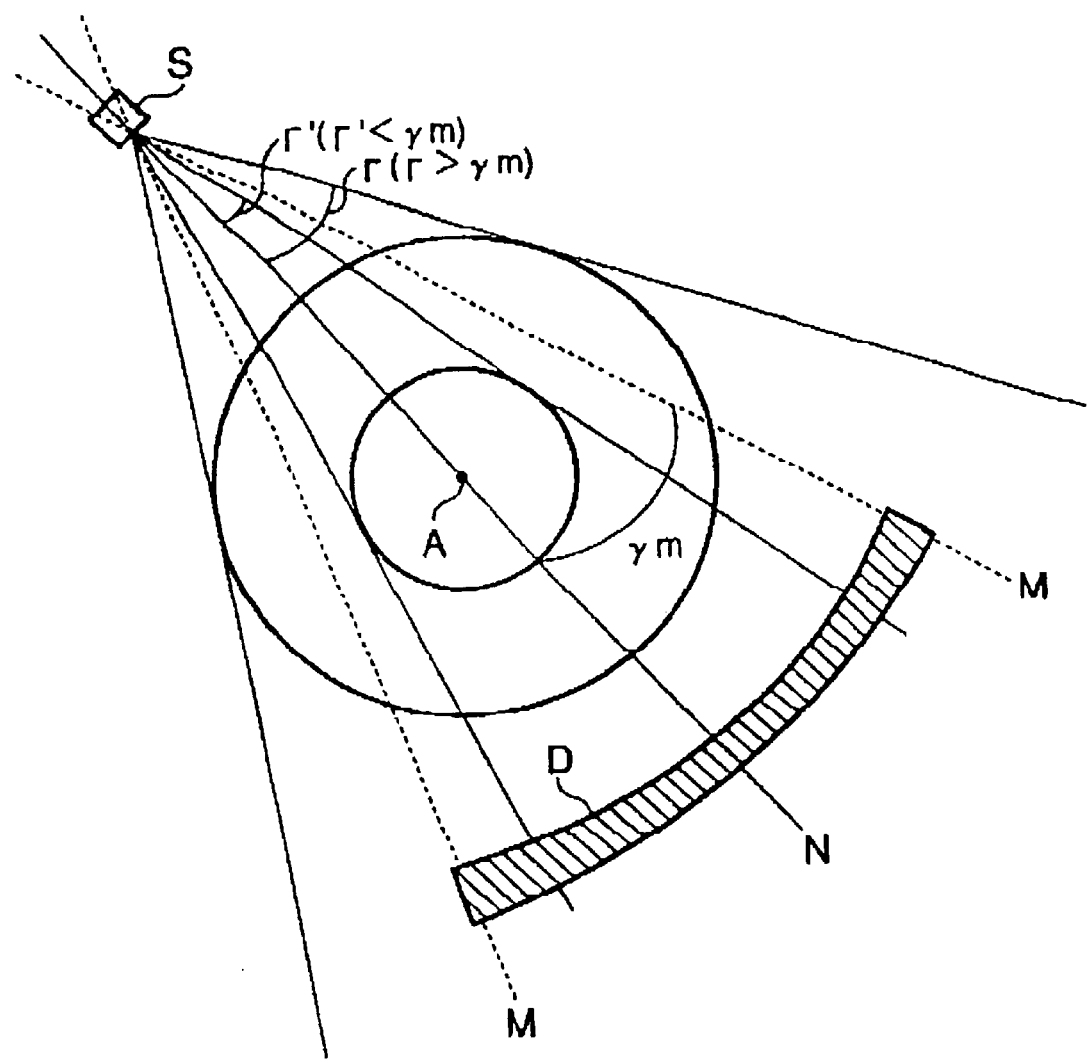
FIG. 2d is a diagram illustrating $\Gamma$ and $\Gamma'$.
Figure 3:
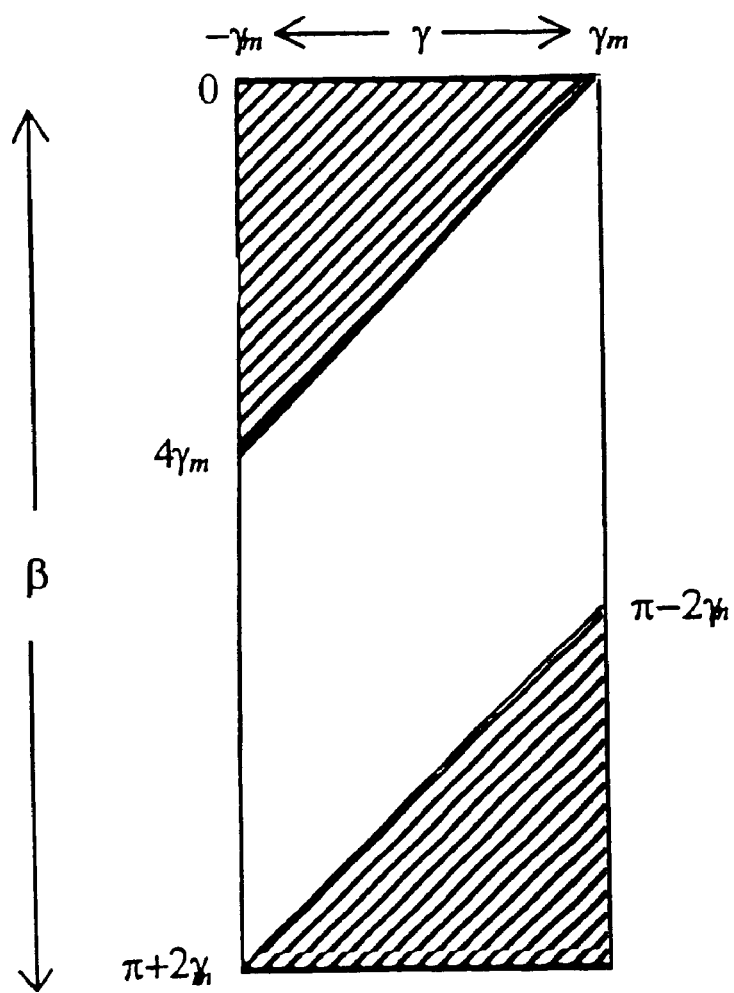
FIG. 3 is a sinogram in Radon space that indicates the angular positions of the source and the fan angles for rays that are sampled twice during the collection of a "minimal complete data set" partial orbit.

The operation of the first embodiment will now be described. As shown in FIG. 2d, the virtual fan angle is spanning less than 180 degrees and more than 0 degrees and is set up to be an angle $2\Gamma$ which is larger than a maximum fan angle $2\gamma m$ angle determined by an element array length of the detector or an angle $2\Gamma$ which is smaller than the maximum fan angle $2\gamma m$. Therefore, a scan is performed by moving gantry G at least the scanning range spanning less than 360 degrees and more than 180 degrees, and 180 degrees plus $2\Gamma$ or 180 degrees plus $2\Gamma'$ (an angle range that an x-ray source rotates in order to acquire projection data for reconstructing an image), actually over the projection range (180 degrees plus $2\Gamma$ or 180 degrees plus $2\Gamma'$, for example, spanning of 180 degrees plus $2\gamma m$), and the projection data spanning of the projection range is collected by the detector D and fan-beam data stored.

In the present invention, data is collected over a scan angle greater than 180 degrees+$2\gamma m$ (step 701) and a "virtual" fan angle $\Gamma$ or $\Gamma'$ is determined (step 702). Although the virtual fan angle is mainly explained as $\Gamma$ in the following explanation, when setting the virtual fan angle as $\Gamma'$, by replacing $\Gamma$ with $\Gamma'$, the explanation can be understood in the same way for the case of setting $\Gamma'$. The angle may be determined from input data to control the span of the source, or may be selected based upon other parameters, such as the scan pitch, by the processor CP or controller CS.

In the present invention, a "virtual" fan angle $2\Gamma$ is determined (step 702). The angle may be determined from input data to control the span of the source, or may be selected based upon other parameters, such as the scan pitch, by the processor CP or controller CS. The virtual fan angle $2\Gamma$ can be used to describe such intermediate partial orbits. This virtual fan angle $2\Gamma$ is used to determine weighting coefficients which are in turned used to weigh certain rays from the collected image data that have been twice-sampled. The weighted rays are themselves used in turn to reconstruct the interior of the object of interest according to any of a number of reconstruction methods. The virtual fan angle $2\Gamma$ is given as one half the difference between the range of angular positions of the source and 180° or $$2\Gamma = \Delta\beta \tag{2}$$

Alternatively, the virtual fan angle $2\Gamma$ can be defined as an angle arbitrarily selected under a condition of 180 degree plus 2Γ being larger than 180 degree and smaller than the scanning range, but larger than the angle 180 degree plus 2γm for collection of the minimum complete data set, or smaller than 180 degree plus 2γm for collection of the minimum complete data set.

Weights are then determined for the collected rays (step 703), the data is weighted (step 704) and the weighted data is used to reconstruct the image using (step 705). Apparatus C performs the weighting and convolution calculations.

Figure 8:
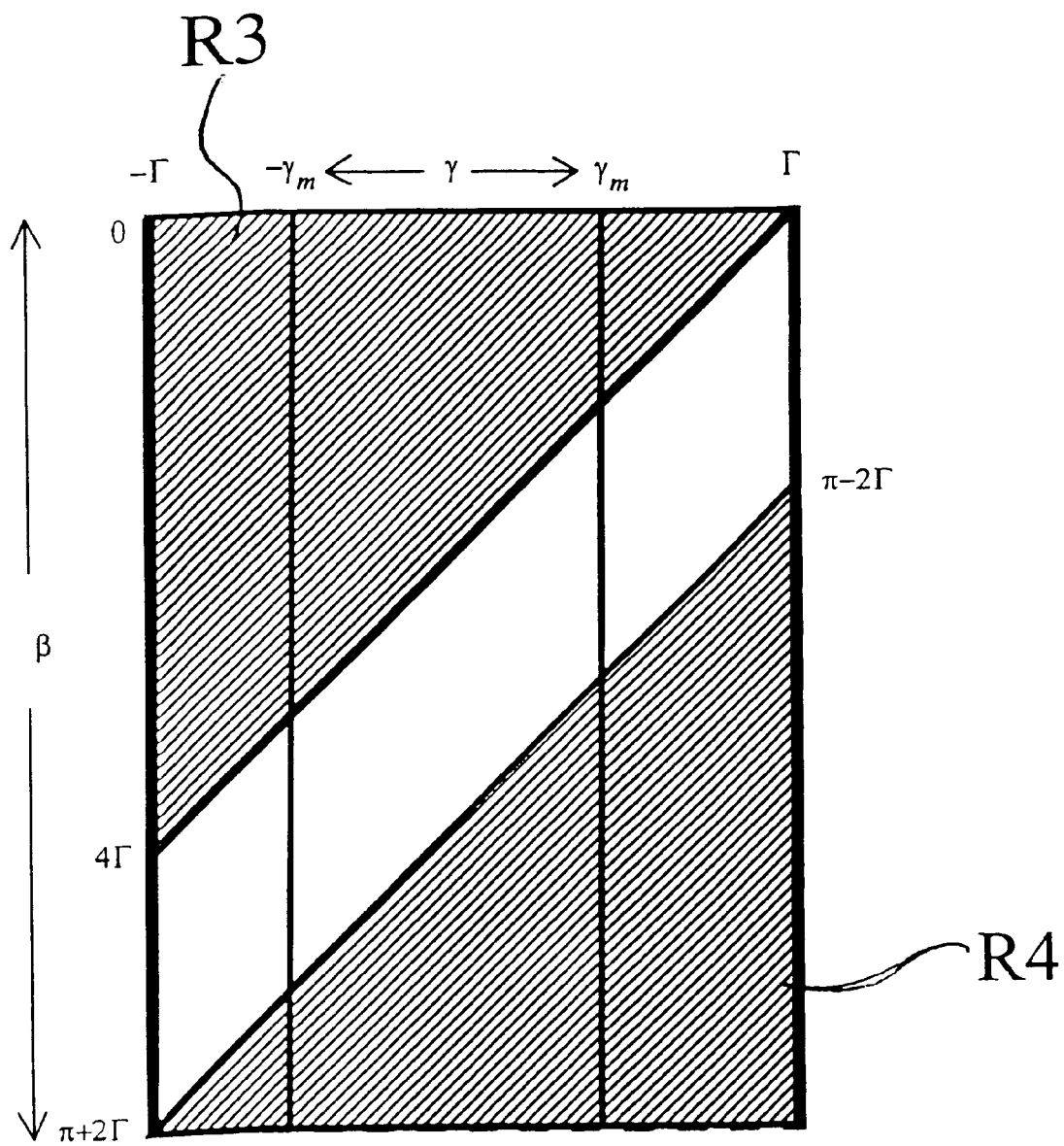
FIG. 8 is a virtual sinogram (graph in Radon space) with the projection range $0<\beta<\pi+\Delta\beta$ and ray-sum angular range within a projection of $-\Gamma\leq\gamma\leq\Gamma$ where $2\Gamma$ is the virtual fan angle of the present invention.
Figure 9:
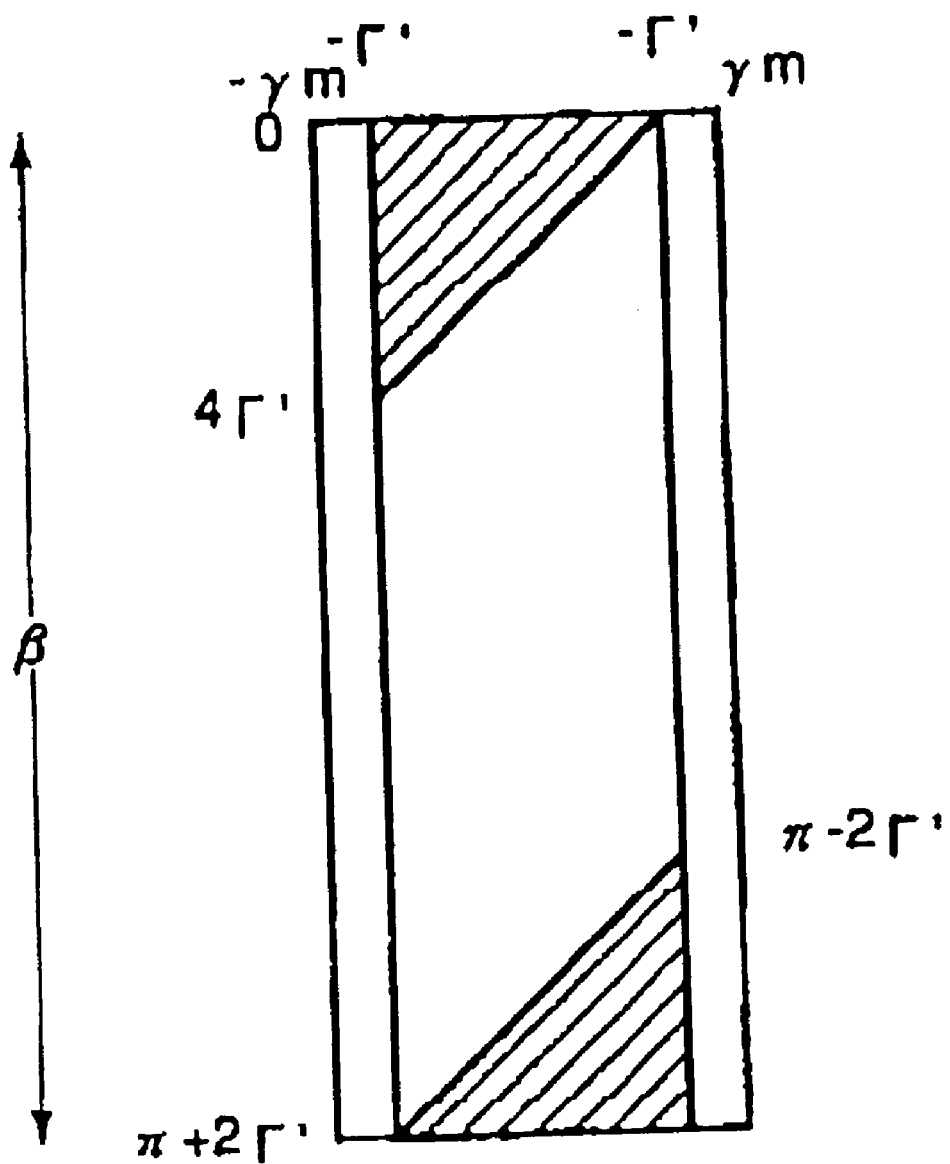
FIG. 9 is a virtual sinogram when the virtual fan angle is set to be $2\Gamma'$ ($\Gamma'<\gamma m$), and the collected projection data is not used for an area $-\gamma m\leq\gamma\leq-\Gamma'$ and $\Gamma'\leq\gamma\leq\gamma m$.

The use of weights determined by using a virtual fan angle results in a virtual sinogram with the projection range $0<\beta<\pi+\Delta\beta$ and ray-sum angular range within a projection of $-\Gamma \leq \gamma \leq \Gamma$ as shown in FIG. 8. This forms a short-scan sinogram with the virtual fan angle of 2Γ. The new Radon space regions $-\Gamma \leq \gamma \leq -\gamma_m$ and $\gamma_m \leq \gamma \leq \Gamma$ for all β consists of virtual data values of zero. As long as the real ray-sum values go to zero at $\gamma = \pm \gamma_m$, then applying the virtual fan angle-derived weights to the virtual sinogram with redundant projections gives the correct reconstruction. In an actual implementation, the regions $-\Gamma \leq \gamma < -\gamma_m$ and $\gamma_m < \gamma \leq \Gamma$ can be ignored as long as the weights are generated with Γ instead of $\gamma_m$. The weights chosen must meet the relation of Equation (1). FIG. 9 is a virtual sinogram when the virtual fan angle is set to be 2Γ' (Γ'<γm), and the collected projection data is not used for an area $-\gamma m \leq \gamma \leq -\Gamma'$ and $\Gamma' \leq \gamma \leq \gamma m$.

There are two interesting limits with this approach. When $\Delta\beta = 2\gamma_m$, the virtual sinogram reduces to the usual Parker short-scan sinogram. When $\Delta\beta = \pi$, this is a 360° (complete orbit) scan but instead of all the ray-sums weighted equally (with 1), the reflection and weight formulas hold. The two triangular regions R3 defined by the points (0,-Γ), (4Γ,-Γ), and (0,Γ) and R4 defined by the points (π+2Γ,-Γ), (π+2Γ,Γ), and (π-2Γ,Γ) in FIG. 8 meet and every ray-sum receives a non-unity weight.

Figure 4:
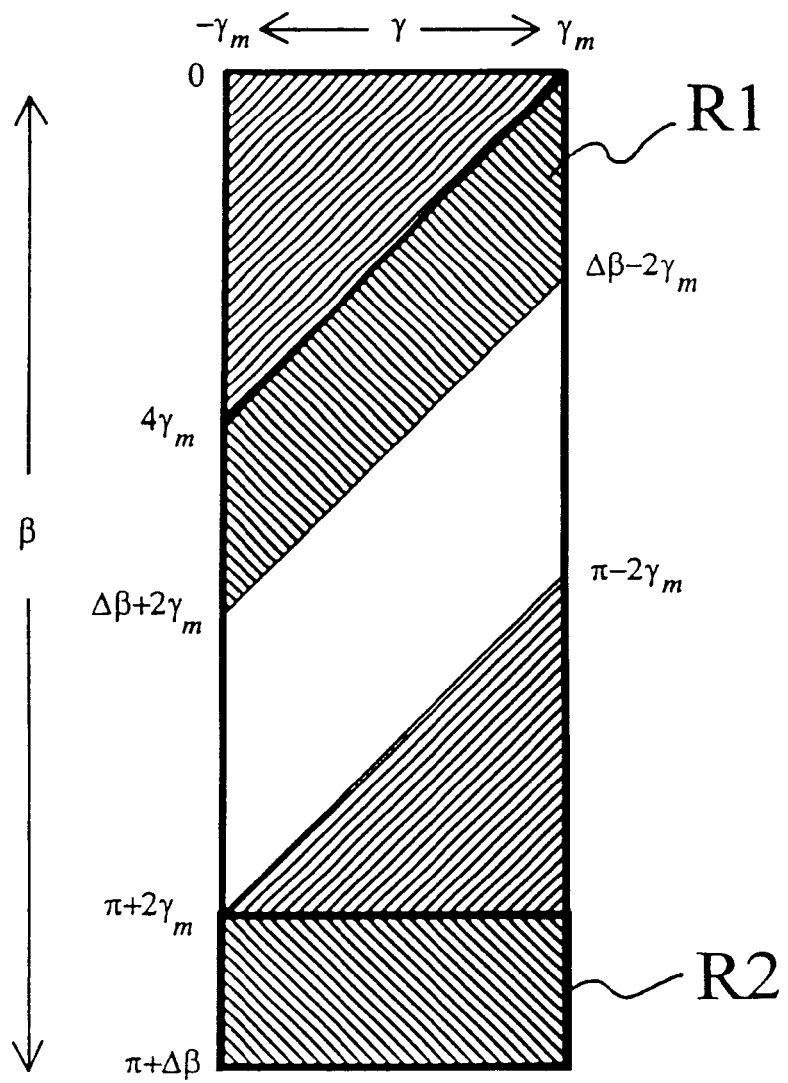
FIG. 4 is a sinogram in Radon space that indicates the angular positions of the source and the fan angles for rays that are sampled twice during the collection of a set of image data using a partial orbit that has a spanned angle intermediate to the spanned angle of a "minimal complete data set" partial orbit and the spanned angle of a complete orbit.

For comparison, FIG. 4 is a sinogram in Radon space that indicates the angular positions of the source and the fan angles for rays that are sampled twice during the collection of a set of image data using a partial orbit that has a spanned angle intermediate to the spanned angle of a "minimal complete data set" partial orbit and the spanned angle of a complete orbit. It becomes apparent that the fraction of twice-sampled rays increases, due both to an increased range $\Delta\beta - 2\gamma_m$ in the angular position of the source β and the redundant sampling of previously sampled rays in this increased range $\Delta\beta - 2\gamma_m$.

Any weighting scheme that satisfies Equation (1) may be used. A specific example is $$w=[x(\beta,\gamma)]=3x^\theta(\beta,\gamma)-2x^1(\beta,\gamma) \quad (3)$$

where $$x(\beta,\gamma) = \begin{cases} \dfrac{\beta}{2\Gamma - 2\gamma} & 0 \leq \beta \leq 2\Gamma - 2\gamma \\ 1 & 2\Gamma - 2\gamma \leq \beta \leq \pi - 2\gamma \\ \dfrac{\pi + 2\Gamma - \beta}{2\Gamma + 2\gamma} & \pi - 2\gamma \leq \beta \leq \pi + 2\Gamma \end{cases} \quad (4)$$

There are numerous conventional methods and devices for performing the reconstruction processing, and such methods may be used in the first embodiment.

Figure 7A:
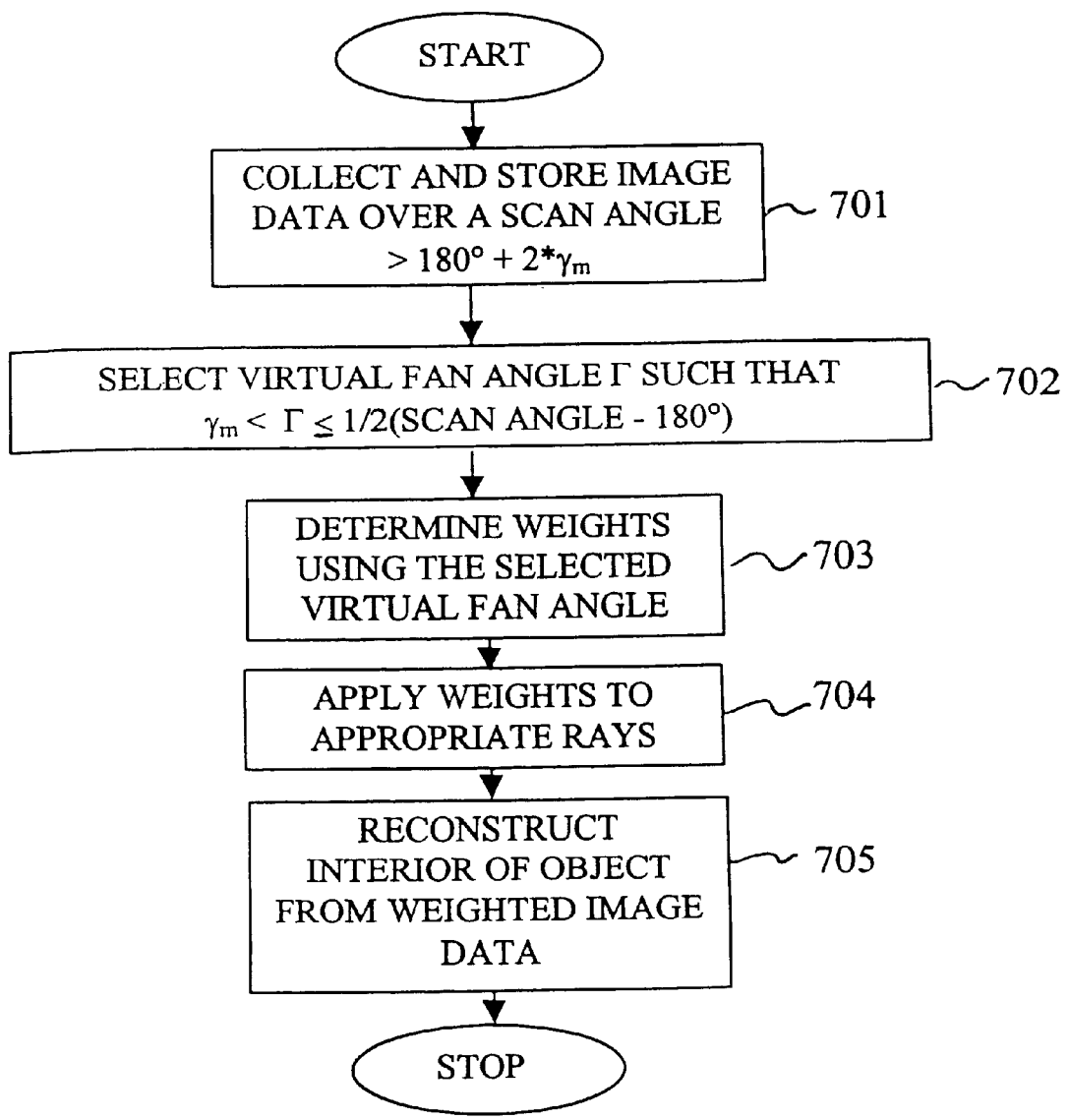
FIGS. 7a and 7b are illustrations of the method according to the invention.
Figure 7B:
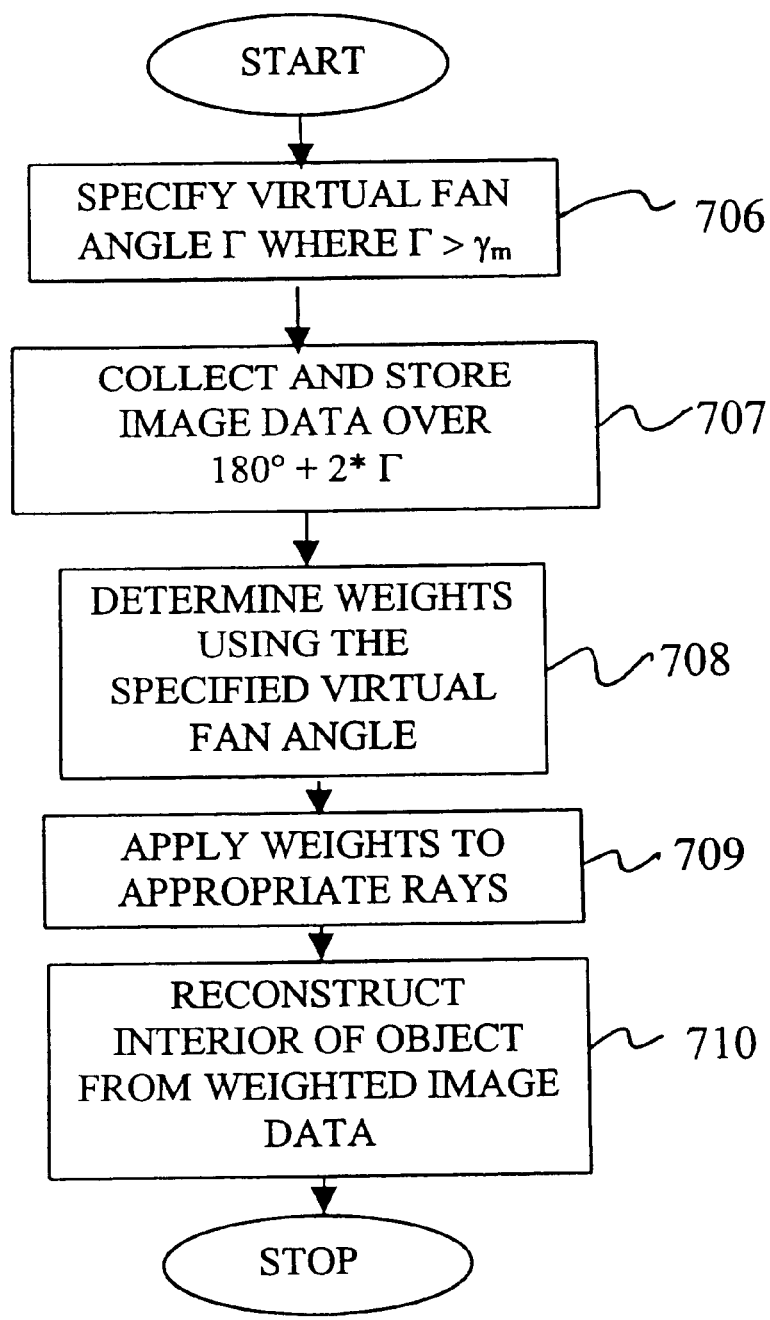

In a modification of the above-described method, shown in FIG. 7b, the virtual fan angle Γ is selected (step 706) and the scan is performed over the range of 180° plus 2Γ (step 707). Weights are determined in step 708 and the data is weighted in step 709, as discussed above with respect to FIG. 7a. The image is reconstructed using the weighted data (step 710), also as discussed above.

EXAMPLE 1

The present invention may be applied to traditional single-slice fan-beam CT systems. The invention can be used to provide a tradeoff between image signal-to-noise (SNR) and temporal resolution. Because the views, labeled by β, are sequential in time and all ray-sums for a given view are at the same time, the β-axis and the time-axis are equivalent. Thus, if images have blur or other patent motion artifacts caused by, for example, breathing, heart beating, or by external moving objects that are introduced to the scan field such as a contrast agent or interventional medical devices like biopsy needles, the blur and artifacts content can be controlled by controlling the number of views (the time range) and in reconstruction. The invention allows a tradeoff between SNR and temporal resolution by allowing a virtual fan angle between $2\gamma_m$ and π, the lower and favoring better temporal resolution and the upper and favoring better SNR. The same reasoning that applies in this example can also be applied to the following two examples.

Referring to FIG. 5, a second embodiment of the system according to the invention is illustrated. On a C-shaped gantry G, an x-ray tube S and an x-ray detector D are mounted facing one another. C-arm gantry systems do not have a well determined fan angle and the angular range of the gantry movement is difficult to control, although it is measured. The range of angular positions of the source can be calculated from the difference between the angular positions of the source β in the first and last frame collected. X-rays emitted from source S are transmitted through a object OB on bed B and are detected by detector D. In one embodiment of the invention, bed B is movably supported, with motion controlled by control/processing apparatus C. In another embodiment, bed B includes a position detector and/or accelerometer (neither shown) for control of and confirmation of the execution of motion instructions indicated by control/processing apparatus C.

Detector D generates exposure data, which is transmitted to control/processing apparatus C. As illustrated here, gantry G is rotatably mounted to a support and rotation mechanism SM containing an internal position detector PD for determining the angular position of the gantry, and control of and confirmation of the execution of motion instructions indicated by control/processing apparatus C. The gantry G may alternatively be suspended from a ceiling mount and may be moved along three axes by combining C-arm rotation, C-arm sliding, and support column rotation. In the case of either ceiling or floor mounting, the support and rotation mechanism SM may be moved laterally and longitudinally. C-arm rotation is used to change the angular position of the source (β in FIG. 1), which is in turn determined using a position detector PD. In the embodiment illustrated here, position detector PD is internal to the C-shaped gantry, although it may also be external or implemented in control/processing apparatus C, as described below.

The operation of the system is controlled by a control/processing apparatus C and data input apparatus IA. Device C typically includes a computer or workstation programmed to carry out the necessary functions and calculations for data processing, and handles storing and processing of the exposure data from device D, weighting of the exposure data from detector D, and controls and monitors the operation of the system, including the movement of the C-arm and image acquisition and data storage and receiving position data used to identify the angular position of the source (β in FIG. 1) from position detector PD. Furthermore, control/processing apparatus C performs reconstruction processing to reconstruct images using a reconstruction processor RP from the exposure data. Control/processing apparatus C includes a memory storage device MS for storing, among other things, data provided by detector D. Control/processing apparatus C also includes a processor CP for performing various calculations and performing functions, such as data weighting.

Input apparatus IA allows an operator to input data or commands to operate or monitor the system. Device IA may typically be a graphical interface having a monitor, keyboard and pointing device. A reconstructed image may also be displayed on the display apparatus DA, which may include, e.g., a monitor and/or a printer.

The most common class of devices for determining the angular position of the source are internally-mounted to the support and rotation mechanism SM or other device that actuates the C-arm gantry G that holds the source S. An example is indicated in FIG. 5 as internal position detector PD. A preferred device to measure the angle of rotation is a rotary encoder.

The system of FIG. 5 operates generally in the same manner as shown in FIGS. 7a and 7b. As indicated by FIG. 1, data collection for a number of rays can be performed simultaneously using fan- or cone-beam CT. The virtual fan angle $2\Gamma$ may be chosen beforehand, and the scan may cover (or exceed) this angular range ($180°+2\Gamma$), or a scan may be performed and $\Gamma$ may be chosen afterwards. There are numerous methods and devices for performing the reconstruction processing. For example, the method described by Feldkamp Davis, and Kress ("Practical Cone-Beam Algorithm", J. Opt. Soc. Am. A1, 612–619, 1984) can be used with the virtual cone-beam angle-weighted rays for the reconstruction of the interior of objects of interest.

EXAMPLE 2

The present invention may be applied to not only rotated type CT but also to rotation angle restriction type C-arm gantries systems such as the Toshiba CAS8000V and CAS10A/AX. Both are digital subtraction angiography (DSA) imagers: the first is ceiling mounted, the latter floor mounted. Both these gantries record the angle (to nearest tenth of a degree) for each frame (a TV-like snapshot of the patient that is digitized) that is collected. Thus, when reconstruction is started, the angles for first and last frame collected are known. This difference is the range and is $2\Gamma+\pi$. In the Toshiba systems described above, three computers are actually used. One handles the data acquisition, one handles CT reconstruction and the third handles the display.

The method according to the invention allows redundant data to be included in CT reconstructions of fan- and cone-beam data without introducing additional complexity to a method such as described by Parker. It should be noted that while the above discussion has been simplified to explain fan-beam exposure, it is equally applicable to cone-beam exposure. In cone-beam exposure, the beam is collimated to have a rectangular cross-section to expose essentially the two-dimensional array of detector elements with a fan angle as defined in FIG. 1.

A third embodiment of the system according to the invention using helical cone-beam CT on a diagnostic CT-gantry is shown in FIG. 6. In this case, the projection data measurement system accommodates an X-ray source S that generates a substantially cone-shaped beam of X-ray flux and a two-dimensional array X-ray detector D consisting of an area array of detector elements, typically 4 rows of detector elements.

The cone-beam system of FIG. 6 also operates generally in the same manner as shown in FIGS. 7a and 7b. As indicated by FIG. 1, data collection for a number of rays can be performed simultaneously using cone-beam CT. The virtual fan angle $\Gamma$ may be chosen beforehand, and the scan may cover (or exceed) this angular range, or a scan may be performed and $\Gamma$ may be chosen afterwards.

For helical cone-beam on a diagnostic CT gantry, the present invention allows more data to be used without extrapolating to where no data exists. For example, consider that voxel represents a tiny volume of the object of interest. Many conventional algorithms call for backprojection of the ray-sum from the focal spot of the x-ray source position through the voxel to the detector. Different voxels are in the cone-beam differently. An algorithm that tries to backproject from one source position through all of the voxels (of a given slice) contains ray-sums that hit and ray-sums that miss the detector, the position that hit and miss depends on helical pitch and FOV. FOV stands for "field of view." In the present invention, more dose data is used, keeping extrapolation to a minimum or eliminating it altogether.

EXAMPLE 3

The invention is applied to cone-beam multi-slice CT apparatus having a maximum fan angle of 49.2°. The helical pitch will affect the selection of $\Gamma$. Let $\beta_1(x,y)$ be the gantry angle when the pixel at x,y enters the cone-beam, and $\beta_2(x,y)$ be the gantry angle when the pixel at x,y leaves the cone-beam. If $\beta=0$ is defined as the gantry angle when the slice is aligned with the focal spot, then all $\beta_1$'s are less than 0 and all $\beta_2$'s are greater than zero. Because of the circular symmetry of the image, the magnitude of the maximum $\beta_1$ is the same as the minimum $\beta_2$, and vice-versa, although not at the same pixel x,y.

The virtual fan angle ($2\Gamma$) may be based upon the angular range that the isocenter pixel (x,y=0,0) is in the cone beam. Artifacts may result in those regions of the slice that are in the cone beam for a smaller gantry angular range than isocenter because of data extrapolation. Here, the fan angle should be selected such that data extrapolation is not necessary. This gives the following conditions for $2\Gamma$:

$$2\Gamma = \begin{cases} 180° & \min(\beta'_2 s) > 180° \\ 2 \times \min(\beta'_\varphi s) - 180° & 114.6° \leq \min(\beta'_\varphi s) \leq 180° \\ 49.2° & \min(\beta'_\varphi s) < 114.6° \end{cases} \quad (5)$$

for each FOV field-of-views in normal slice direction and helical pitch. Note that 114.6° satisfies 49.2°=2×114.6°−180°, where 49.2° is the actual fan angle of the scanner. In order not to have data extrapolation, $2\Gamma$ must be greater than 49.2°. The following table on summarizes these findings for the five FOV's of the scanners and three likely helical pitches. Entries in italics will have data extrapolations for some pixels in the reconstructed image.

| FOV (mm) | Helical Pitch | 2Γ |
|---|---|---|
| 500 | 0.625 | 156° |
|  | 1.0 | 49.2° |
|  | 1.25 | 49.2° |
| 400 | 0.625 | 180° |
|  | 1.0 | 60° |
|  | 1.25 | 49.2° |

-continued

| FOV (mm) | Helical Pitch | 2Γ |
|---|---|---|
| 320 | 0.625 | 180° |
| | 1.0 | 88° |
| | 1.25 | 49.2° |
| 240 | 0.625 | 180° |
| | 1.0 | 108° |
| | 1.25 | 50° |
| 180 | 0.625 | 180° |
| | 1.0 | 126° |
| | 1.25 | 64° |

Helical pitch is determined as table travel during one revolution of the source divided by the full width of the detector as projected as isocenter.

In the case of reconstructing a 500 mm object scanned at a helical pitch of 1, there is no data extrapolation for any pixel less than 200 mm from isocenter (because the entry for 2Γ for the 400 mm FOV, helical pitch of 1, is greater than 49.2°). Similarly, at a pitch of 1.25, there is no data extrapolation for any pixel less than 120 mm from isocenter; however, some pixels more than 120 mm from isocenter will use data extrapolations.

In this example, the method according to the invention should be less noisy. Compared to half-scanning (HS) the improvement is given by $$\frac{\text{Noise with } HS}{\text{Noise with } MHS} = \sqrt{\frac{180 + 2\Gamma}{180 + 49.2}}. \tag{6}$$

However, reconstruction time is longer by $$\frac{360}{180 + 2\Gamma}. \tag{7}$$

because of the additional views to backproject. To keep scaling consistent, the final image may require an additional scale factor of $$\frac{180 + 2\Gamma}{180 + 49.2} \tag{8}$$

The present invention provides for selecting a virtual angle based upon a helical pitch providing desired image characteristics such as image contrast of subtle features in the image.

The present invention may also be implemented as software to perform the various functions and calculations described above. The software is stored in the processor C in FIG. 5 or in the system controller CS or processor CP of FIG. 6. The software may be installed on a disk to implement the invention as a computer program product.

For example, the half scanning reconstruction method employing the virtual fan angle as mentioned above is applicable to the ASSR method described in patent disclosure (KOKAI) no. 8-187240. The ASSR method is a method for reconstructing an image from approximate projection data of the x-ray path (ray), in which the approximate projection data of the x-ray path corresponding to a selected virtual plane is obtained from actually collected projection data in multi-helical CT device. For example, the method can achieve to reconstruct a slanting tomographic image by selecting the virtual plane along a helical orbit of an x-ray source and be applied to the half scanning reconstruction method.

The half scanning reconstruction method that employs the virtual fan angle mentioned above is also applicable to Dynamic CT. The Dynamic CT is a method for reconstructing images by shifting a scan range (an angular range like 30 degrees or 60 degrees less than 180 degrees) required for reconstructing an image while an x-ray source is rotated and is a method for reconstructing continuous images of high time resolution. The method also can employ the above-mentioned half scanning reconstruction method using the virtual fan angle.

In another embodiment, the channel angle is chosen as a function of the field-of-view (FOV). This embodiment further increases the helical scan pitch. In this embodiment only valid ray-sums are preferably used. In other words, extrapolation is eliminated or minized. A ray-sum is valid, that is, measured, if γ and n are locations within the physical detector array. The following table illustrates the maximum minimum channel angle and the backprojection range for different FOV's.

| FOV (mm) | Channel Angle ($\gamma_m$) | Range (180° + 2 $\gamma_m$) |
|---|---|---|
| 500 | 24.6° | 229.2° |
| 400 | 19.5° | 219° |
| 320 | 15.5° | 211° |
| 240 | 11.5° | 203° |
| 180 | 8.6° | 197.2° |

Figure 10A:
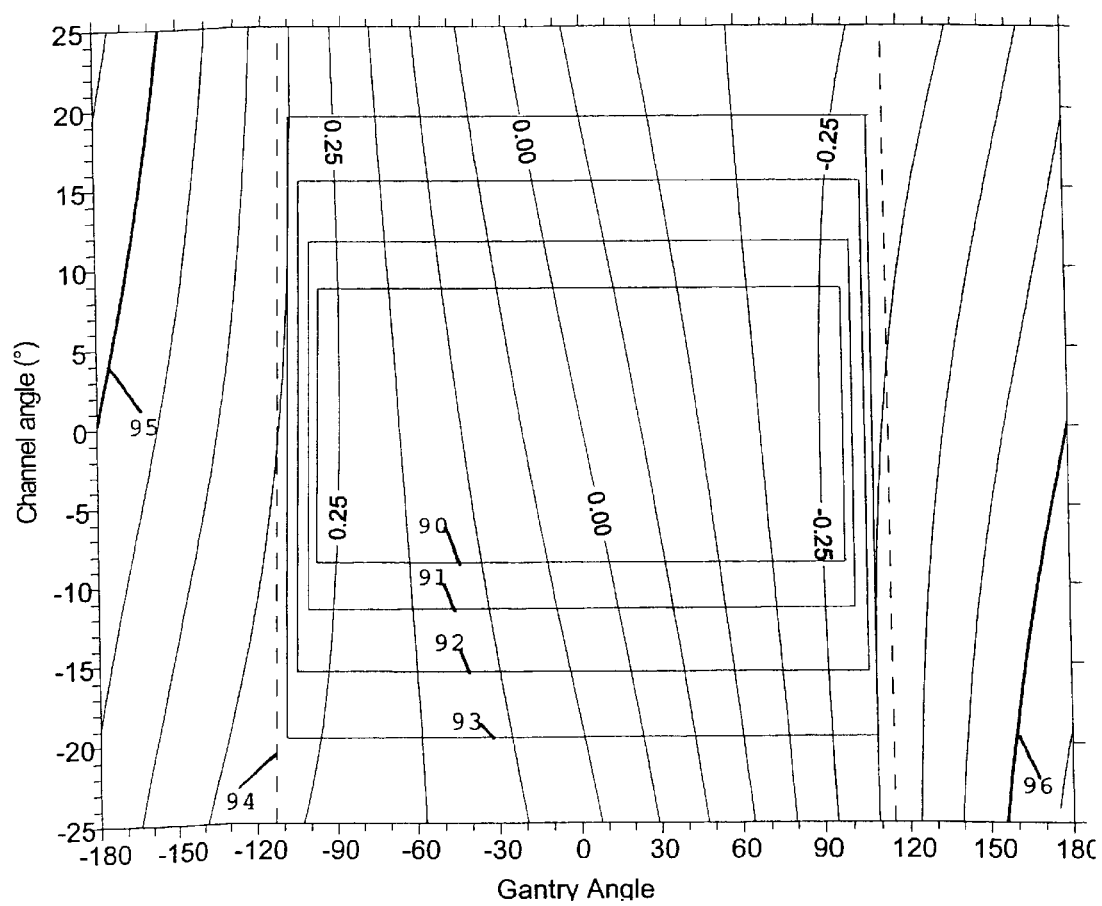
FIG. 10a is a contour map for a helical pitch ratio of one.
Figure 10B:
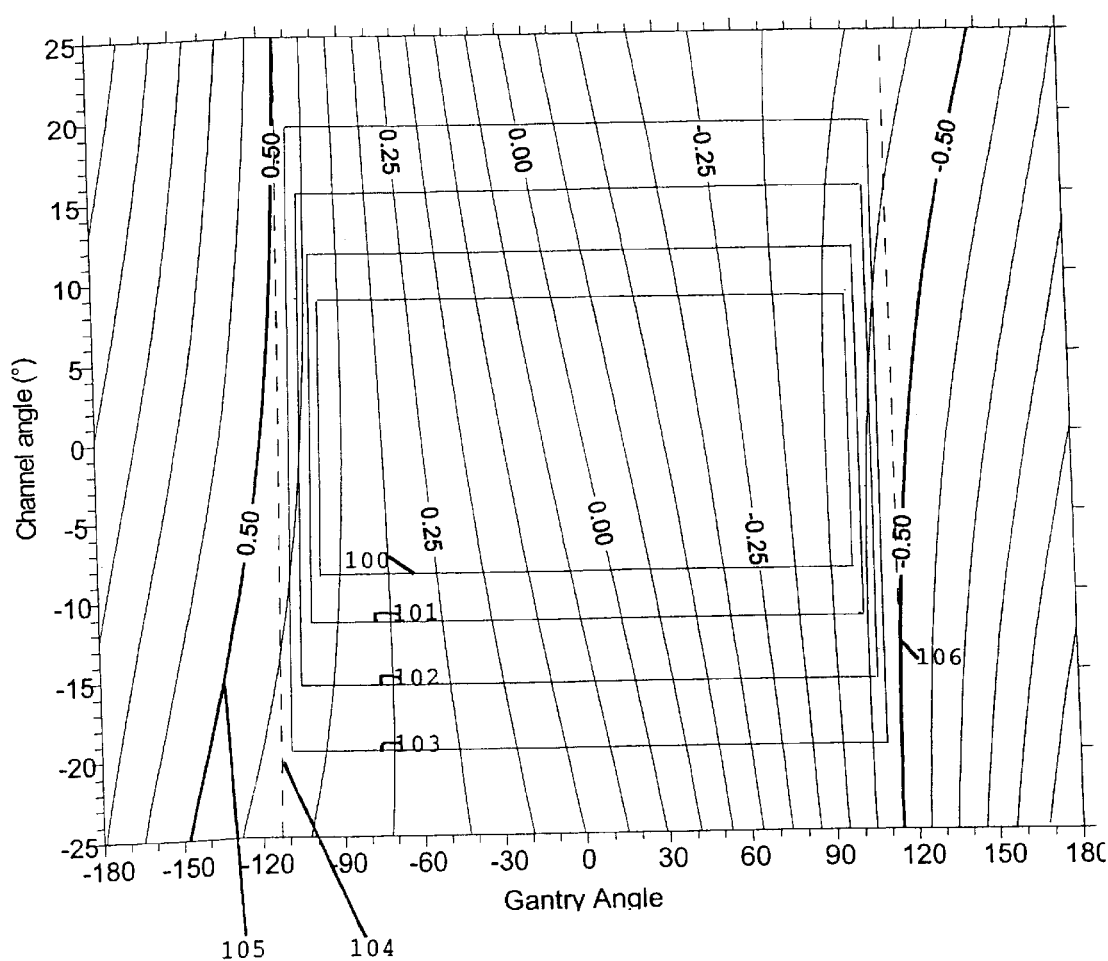
FIG. 10b is a contour map for a helical pitch ratio of 1.5.

Contour plots illustrating the reconstruction area are shown in FIG. 10a, for a normalized helical pitch of 1.0. The contour lines represent the normalized line segment value for the ray-sum from the source position indicated on the horizontal axis with channel angle indicated on the vertical axis. Regions 90–94 correspond to the 180, 240, 320, 400 and 500 mm FOVs. The conventional approach, normal "Parker" weights (using 229° as 180°+fan angle} would extend to the vertical dashed lines 94. Regions outside of contours 95 and 96 would require extrapolation. FIG. 10b illustrates contours for a normalized helical pitch of 1.5. Regions 100–104 correspond to the 180, 240, 320, 400 and 500 mm FOVs, the conventional approach would extend to dashed lines 104, and regions outside of contours 105 and 106 would require extrapolation.

It will now be described in more detail how the helical pitch is further increased. Conventionally, 4-row detector CT systems have used two-dimensional reconstruction algorithms. With larger row detectors, it has been found that three-dimensional backprojection produces better quality images. As detectors get larger, the reconstruction problem approaches the fully three-dimensional problem. Since the cone angle in CT is not too large, a reconstruction algorithm which is a modification of helical Feldkamp reconstruction is possible, where the maximum helical pitch is determined by two-dimensional arguments. This embodiment is applicable to detectors having a large number of rows, as many as 512.

Backprojection follows the straight-line ray-sum from the focal spot of the x-ray source through a pixel of interest in the image volume and onto the two-dimensional detector array. Typically, the processed signal at this location in the detector array is weighted and added to the contents of the voxel. This is repeated for all voxels and for a range of x-ray source angles. For helical, cone-beam scanning, the relation between a voxel and a location in the detector array for a given source angle is given by $$\gamma(\beta, x, y) = \sin^{-1} \frac{x\cos\beta + y\sin\beta}{L(\beta, x, y)} \quad (9)$$

$$\alpha(\beta, x, y, z) = \tan^{-1} \frac{[\beta - \beta_o(z)]H}{2\pi L(\beta, x, y)} \quad (10)$$

where:

$\gamma$ is the fan angle (in the x-y plane) of the ray-sum, $\alpha$ is the cone angle of the x-ray sum, $\beta$ is the x-ray source angle, $\beta_o$ is the source angle when the focal spot position is in the image slice at z, x, y, z is the coordinate of an image pixel, H is the helical pitch: table travel per rotation of the source, and $L(\beta,x,y) = [(R \sin \beta + x)^2 + (R \cos \beta - y)^2]^{-1/2}$ L is the distance from the focal spot to the pixel x, y, z times the cosine of the cone angle, R is the radial distance of the focal spot to isocenter. The coordinate system moves with the patient/table so that each image slice is at a fixed z.

Multi-row CT-scanners have detector arrays that are sections of a cylinder, focused on the source; thus equal angular increments $\Delta\gamma$ and equal axial linear increments separate the individual sensor elements. Therefore, $\gamma$ is a natural coordinate for the ray-sum but (10) is changed in favor of detector or rows (also known as slice or segments), $$n(\beta, x, y, z) = \frac{[\beta - \beta_o(z)]R}{2\pi L(\beta, x, y)} r_H \quad (11)$$

where n is the relative detector row, $$-\frac{1}{2} \le n \le \frac{1}{2} \quad (12)$$

and $$r_H = \frac{H}{W} \quad (13)$$

with W as the full axial height of the detector array as projected at isocenter. Thus, $r_H$ is the normalized helical pitch ratio.

A ray-sum is valid, that is, measured, if $\gamma$ and n are locations within the physical detector array. For helical, cone-beam CT, the equation is (12) combined with (11). Equation (12) may be solved with n=±½ for the surfaces of $\beta_{1,2}$ as a function of voxel position x, y, z. $\beta_{1,2}$ represents the source angular position when the voxel x, y, z enters and then leaves the cone-beam. These surfaces are warped, depending on helical pitch. The difference of the two surfaces shows that up to a normalized helical pitch ratio of 2, all voxels have at least 180° range of coverage. However, the voxels do not have the same 180° range of coverage. This implies that a reconstructional algorithm could exist that uses only valid ray-sums up to a normalized helical pitch ratio of 2.

Figure 11:
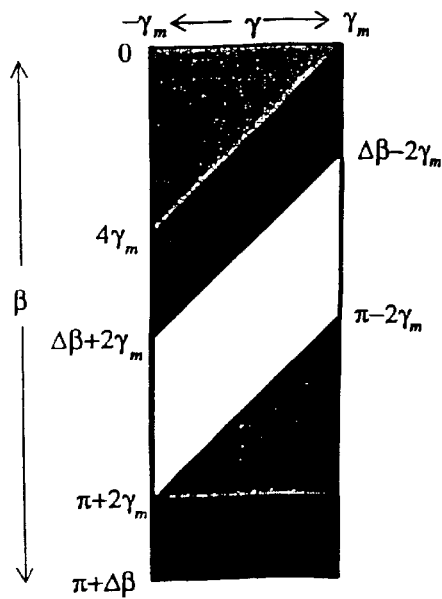
FIG. 11 is a sinogram of one row of a detector.

The helical pitch determines how long a given voxel is irradiated. Obviously, the higher the pitch, the less the voxel is within the rotating cone-beam and vice versa. In this embodiment of the invention, the weighting scheme described above is adapted for helical cone-beam scanning. In a sinogram from a single detector row, suppose all the voxels of a given slice are in the cone-beam for at least $\pi+\Delta\beta$ (as shown in FIGS. 10a–10b). The weighting scheme, based on Parker's half-scan method as discussed above, uses the virtual fan-angle, $2\Gamma$, such that $2\Gamma=\Delta\beta$, as shown in FIG. 11. The same weights are the same as in half-scanning (Parker and Crawford) for the redundant (in two-dimensions) triangles but with $2\Gamma$ as the fan-angle.

Under the condition that valid rays-sums are used, as described above, and that all voxels in a slice are reconstructed over the same angular range of the source, then the relation between the angular range of the source used in the reconstruction, the helical pitch, and the field-of-view FOV (R is the source radius) can be shown to be:

$$\beta_2 - \beta_1 = \pi + 2\Gamma = \frac{2\pi}{r_H} \times \left(1 - \frac{FOV}{2R}\right) \quad (14)$$

The minimum and maximum values for the helical pitch correspond to when the virtual fan-angle approaches $\pi$ and $2\gamma_m$, the true fan-angle, respectively:

$$r_H(\min, FOV) = 1 - \frac{FOV}{2R} \quad (15)$$

$$r_H(\max, FOV) = \frac{2\pi}{\pi + 2\gamma_m} r_H(\min, FOV) \quad (16)$$

It is thus possible to increase the helical pitch. Keeping the helical pitch below the limit given in equation (14) assures that all ray-sums that go into making the image are valid ray-sums in a three-dimensional sense, although weighting derived from two-dimensional arguments is used. Referring again to FIG. 11, for the smaller FOV's, the ray-sum values in the region $$\sin^{-1}\left(\frac{FOV}{2R}\right) < |\gamma| < \gamma_m \quad (17)$$

are zero. Note that $$\gamma_m = \sin^{-1}\left(\frac{FOV_{\max}}{2R}\right) \quad (18)$$

where $FOV_{max}$ is the maximum field-of-view for the scanner. This implies that the range of validity for equation (16) is increased. Instead of $r_H$(max, FOV) being given by when the virtual fan-angle reaches $2\gamma_m$, it is given by when the virtual fan-angle reaches $$2\sin^{-1}\left(\frac{FOV}{2R}\right) \quad (19)$$

Therefore, equation (16) becomes $$r_H(\max, FOV) = \frac{2\pi}{\pi + 2\sin^{-1}\left(\frac{FOV}{2R}\right)} r_H(\min, FOV) \quad (20)$$

The ratio of the increase is $$\frac{r_H(\max, FOV)}{r_H(\min, FOV)} = \frac{\pi + 2\sin^{-1}\left(\frac{FOV_{\max}}{2R}\right)}{\pi + 2\sin^{-1}\left(\frac{FOV}{2R}\right)} \quad (21)$$

Figure 13:
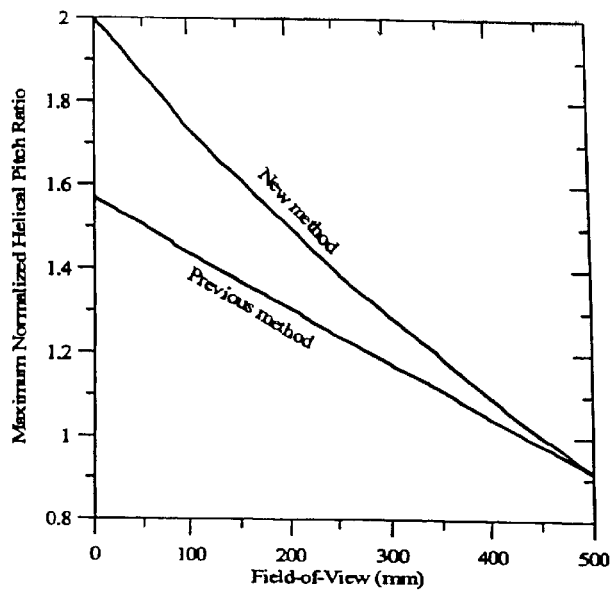
FIG. 13 is a diagram comparing the helical pitch according to the invention with a conventional helical pitch.
Figure 12:
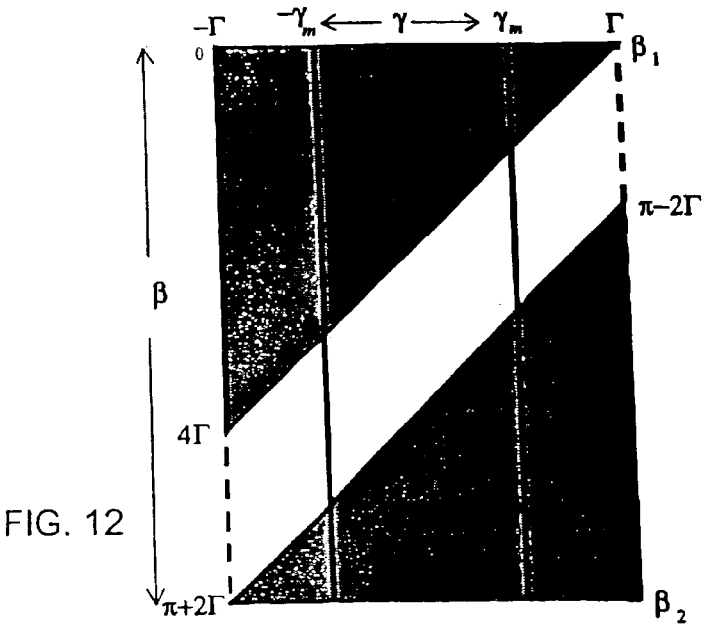
FIG. 12 is a sinogram derived using a virtual fan angle.

FIG. 12 compares the maximum according to the invention for the helical pitch with the previous calculations as a function of FOV. In FIG. 12, a sinogram is shown where the fan angle is increased to the virtual fan angle 2Γ. The shaded regions contain redundant information. FIG. 13 illustrates the efficacy of the higher helical pitch with a computer simulation of a 16-row cone beam CT-scanner using clinical images. Curve 130 illustrates the helical pitch for the conventional Parker-type weighting while curve 131 illustrates the helical pitch according to the invention. Clearly, the present invention offers higher helical pitches while producing good quality images.

In a further embodiment of the invention, time-shifting is included where the span is shift along a time axis. This is described in application Ser. No. 09/450,121, the contents of which are herein incorporated by reference.

In another embodiment of the invention ASSR is included where a CT image is reconstructed from projection data of an x-ray path along a virtual plane in multi-helical CT. This is described below and in Japanese application Serial No. 7-2512, the contents of which are herein incorporated by reference.

Figure 14:
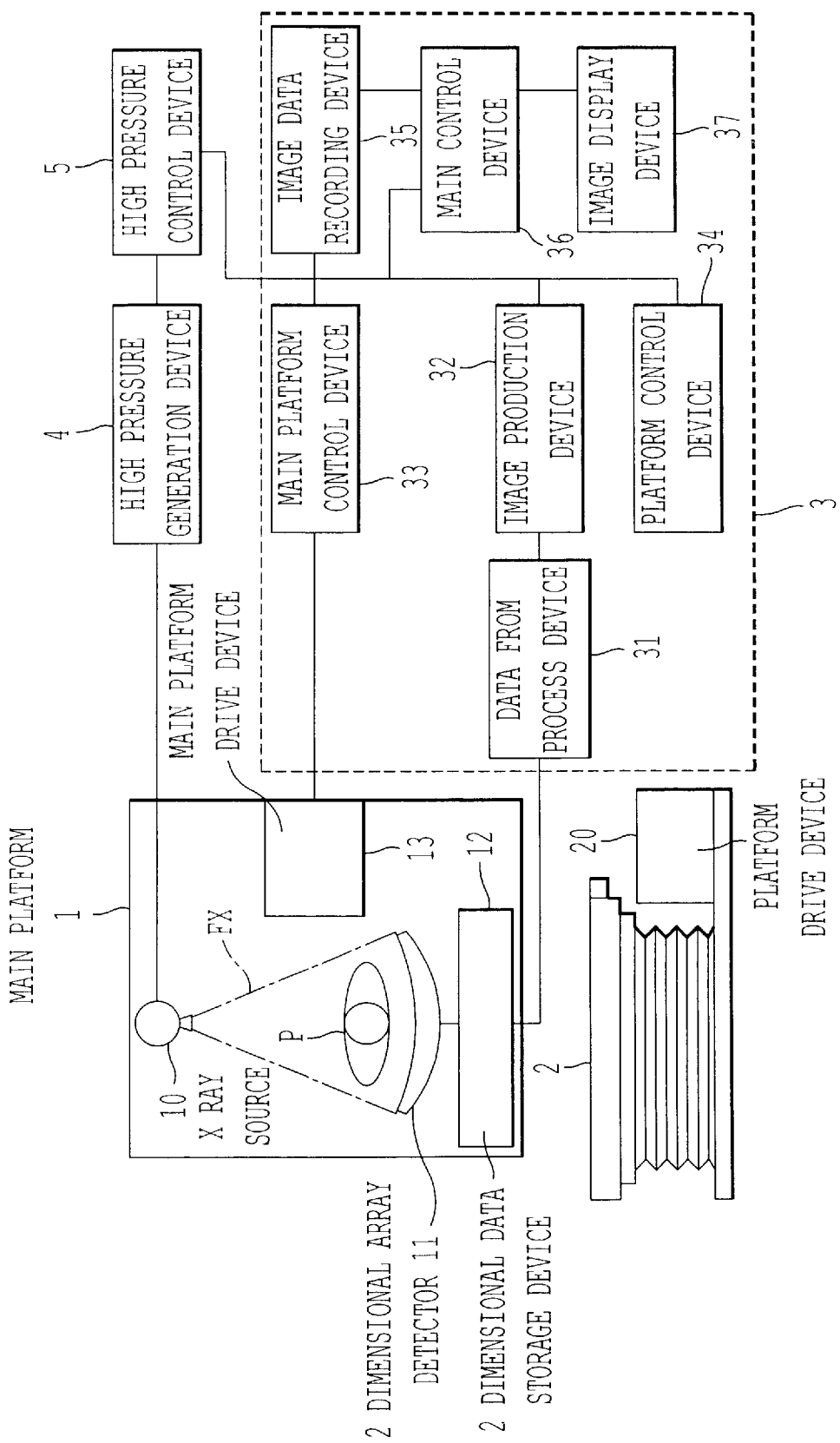
FIG. 14 is a diagram of system used for ASSR.

This embodiment provides a helical scan CT using a two-dimensional arrayed detector, which is capable of generating reconstructed images with a few artifacts by simple processes. In this embodiment, as shown in FIG. 14, a computed tomographic imaging apparatus for collecting projection data by helical scan using a two-dimensional arrayed detector 11 is characterized by extracting approximate projection data for an X-ray path approximate to the position of an arbitrarily determined virtual plane from two-dimensional projection data actually collected and using the approximate projection data to reconstruct a reconstructed image.

In a conventional helical scan system having a one-dimensional detector, the X-ray source is moved on a helical trajectory, so that most of projection data on a reconstruction plane needs to be approximately generated by interpolation using a linear interpolation process and the like. Hereafter, the generated data is referred to as approximate projection data. For reconstruction, data for a rotation is substantially needed, and thus when an area having a 10-cm thickness, for example, is needed as slice data in a two-millimeter thickness, 50 rotations of scans have been required.

In a so-called dual-slice helical system where the one-dimensional detectors are arranged in two rows, the data collection rate is two times as fast as the above-described system in principle. To make progress in this system, it is thought to arrange the one-dimensional detectors into multi-row, by X-ray paths between the rows are not assumed to be in parallel. If images are simply reconstructed as a multi-slice at every row with supposing that the X-ray paths are in parallel, the resulting images have many artifacts. Techniques overcoming these problems have not been proposed at present, and therefore, it is concluded that this system is limited to doubling the speed at most.

In a cone-beam scan system, a perfect reconstruction is feasible in principle when an object is fully contained in cone beam. However, in the case where the object is not fully contained in the cone beam, appropriate solutions for reconstruction have not been proposed.

As described above, there does not exist a simple reconstruction method with fewer artifacts in the helical scan CT using the two-dimensional arrayed detector. This embodiment provides a helical scan CT using a two-dimensional arrayed detector capable of generating reconstructed images with few artifacts by simple processes.

In a computed tomographic imaging apparatus for collecting projection data by helical scan using a two-dimensional arrayed detector, approximate projection data for an X-ray path approximate to the position of an arbitrarily determined virtual plane is extracted from two-dimensional projection data actually collected and a reconstructed image is reconstructed by using the approximate projection data.

According to this embodiment, the approximate projection data for the X-ray path approximate to the position of the arbitrarily determined virtual plane is extracted from the two-dimensional projection data actually collected and the approximate projection data is used to reconstruct a reconstructed image. Therefore, a reconstructed image with fewer artifacts can be generated by simple processes in the helical scan CT using the two-dimensional arrayed detector.

According to this embodiment, the approximate projection data for the X-ray path approximate to the position of the arbitrarily determined virtual plane is extracted from the two-dimensional projection data actually collected and the approximate projection data is used to reconstruct a reconstructed image. Therefore, a reconstructed image with fewer artifacts can be generated by simple processes in the helical scan CT using the two-dimensional arrayed detector.

EXAMPLE

Figure 16:
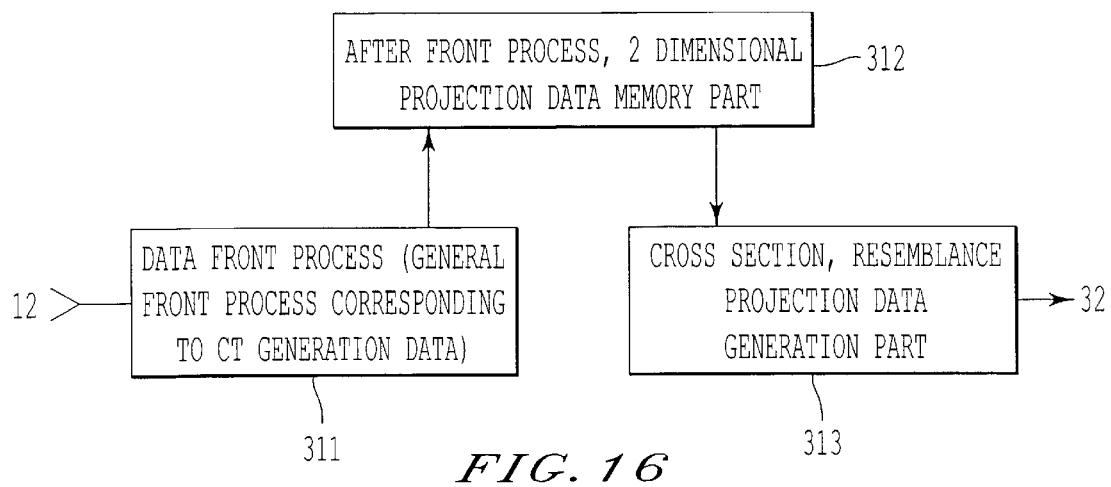
FIG. 16 is a block diagram illustrating the data preprocessor shown in FIG. 14.

Hereafter, one example of the CT imaging apparatus will be described. FIG. 14 is a structural diagram of a CT in the embodiment. FIG. 16 is a block diagram of a data preprocessor shown in FIG. 14. The CT is roughly configured of a gantry 1, a bed 2, and a console 3. In the central part of the gantry 1, a cylindrical hollow portion is provided and an object P is inserted as it is placed on the bed 2 in scanning. In addition, the horizontal axis parallel to the body axis direction of the object P is defined as the Z-axis, the vertical axis is the Y-axis, and the horizontal axis orthogonal to the Z-axis is the X-axis. The bed 2 is configured to be movable as it is driven by a bed drive unit 20 with the object P placed thereon. An X-ray source 10 receives high voltage from a high voltage generator 4 and it irradiates a fan-like X-ray beam FX. A spread angle of the fan-like X-ray beam FX is called a fan angle; it is set to ±A degrees from side to side centering the central axis, 2A degrees in total. As a typical example, the fan angle is set to 50 degrees.

A two-dimensional arrayed detector 12 is constructed by arranging detectors for detecting X-rays passed through the object P as electrical signals in a two-dimensional manner. The X-ray source 10 and the two-dimensional arrayed detector 12 are supported by a rotation mechanism and a slipring mechanism (not shown) in such a manner that they are continuously rotatable around the object P as they face each other. This rotation is driven by a gantry drive unit 13. The output from the two-dimensional arrayed detector 12 is integrated with respect to time by a two-dimensional data collector 12, and it is digitized and collected as projection data. A high voltage generator 4, the gantry drive unit 13, and a bed drive unit 20 are controlled by a high voltage controller 5, a gantry controller 33, and a bed controller 34, respectively.

The projection data from the two-dimensional data collector 12 is sent to a data preprocessor 31 shown in detail in FIG. 16, in which the data is subjected first to a general preprocess such as Log conversion (logarithmic transformation) in a data preprocessing part 311, and thereafter stored in a preprocessed two-dimensional projection data storage part 312. A slanting tomographic plane approximate projection data generating part 313 uses the preprocessed projection data, and generates approximate projection data necessary to reconstruct images regarding a slanting tomographic plane. An image reconstruction unit 32 reconstructs images (images of the slanting tomographic plane) from the approximate projection data generated in the slanting tomographic plane approximate projection data generating part 313. For the reconstruction process, a so-called half scanning reconstruction method capable of reconstructing images from projection data corresponding to 180 degrees is adopted.

The tomogram data is sent to an image display unit 37 for display through a main controlling part 36, and it is sent to an image data storage unit 35 for storage. The main controlling part 36 controls the high voltage controller 5, the gantry controller 33, and the bed controller 34, and it executes helical scan.

Figure 15A:
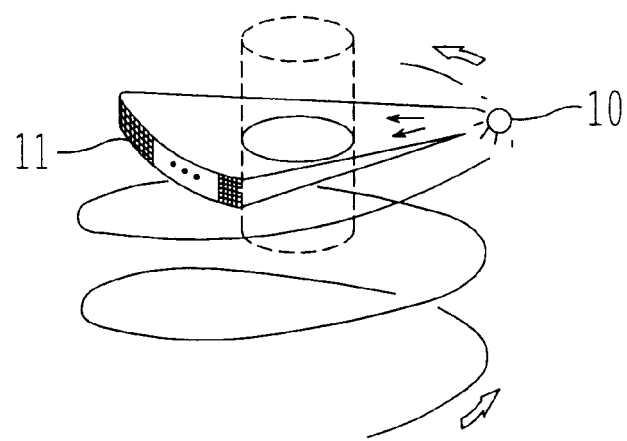
FIGS. 15a and 15b are diagrams illustrating the helical trajectory of an X-ray source in helical scan.

Next, the operation of the embodiment will be described. In addition, the moving coordinate system moving with the object P will be defined for convenience of explanation. In this moving coordinate system, the X-ray source 10 is to move on the helical trajectory as shown in FIG. 15a in helical scan. In the actual movement, the object P is moved in one direction by the bed 2 while the X-ray source 10 and the two-dimensional arrayed detector 11 are continuously rotated. Here, special terms addressed in the following explanation will be defined.

Actual projection data: projection data actually collected by each of detectors in the two-dimensional arrayed detector 11;

Virtual projection data: ideal projection data needed to reconstruct images on the reconstruction plane (here, it is defined as the slanting tomographic plane), i.e. the projection data on the X-ray path (it is referred to as virtual path) contained in the reconstruction plane. Such a virtual projection data does not exist in helical scan with a few exceptions.

Approximate projection data: projection data on the X-ray path (it is referred to as approximate path) in an X-ray beam FX most approximate to the virtual path. The approximate projection data may exist as actual projection data, and it may not exist. When it does not exist, it is generated from the actual projection data close to the approximate path by interpolation (distance interpolation). The approximate projection data is generated one by one at every direction of irradiating X-rays from the X-ray source 10 (it is defined as fan interior angle) on each rotation angle of the X-ray source 10.

Figure 15B:
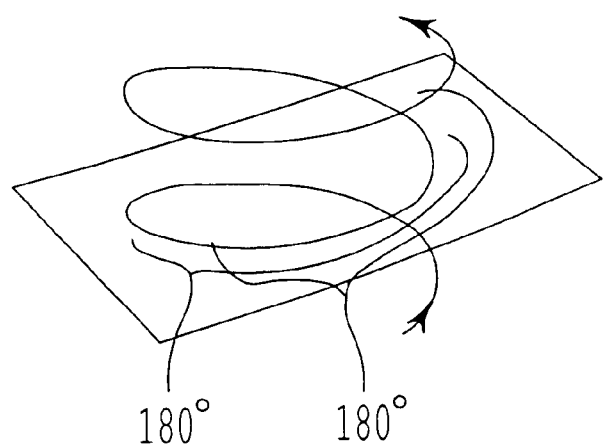

In helical scan, a single plane cannot be defined by a plurality of X-ray paths required for reconstruction. One of the features of the embodiment is in that the slanting tomographic plane (reconstruction plane) inclined relative to the Z-axis is set with respect to a group of X-ray paths for a half rotation of the X-ray source 10 and projection data for this half rotation is used to reconstruct images (see FIG. 15b). Accordingly, the shift of the curved plane drawn by the group of X-ray paths for a half rotation from the reconstruction plane is small, and thus images with fewer artifacts can be reconstructed. Moreover, the feature of the embodiment is in that the slanting tomographic plane that minimizes artifacts, i.e. minimizes the shift, is set with respect to the group of X-ray paths for a half rotation, and approximate paths are set. The approximate paths are specified by the rotation angle of the X-ray source 10, the fan interior angle, and the Z-position.

Figure 17:
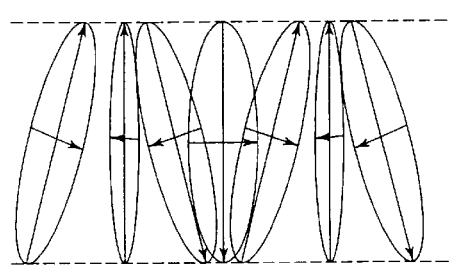
FIG. 17 is a diagram illustrating changes of the slanting tomographic plane shifted at an angle of 90 degrees respectively.
Figure 20:
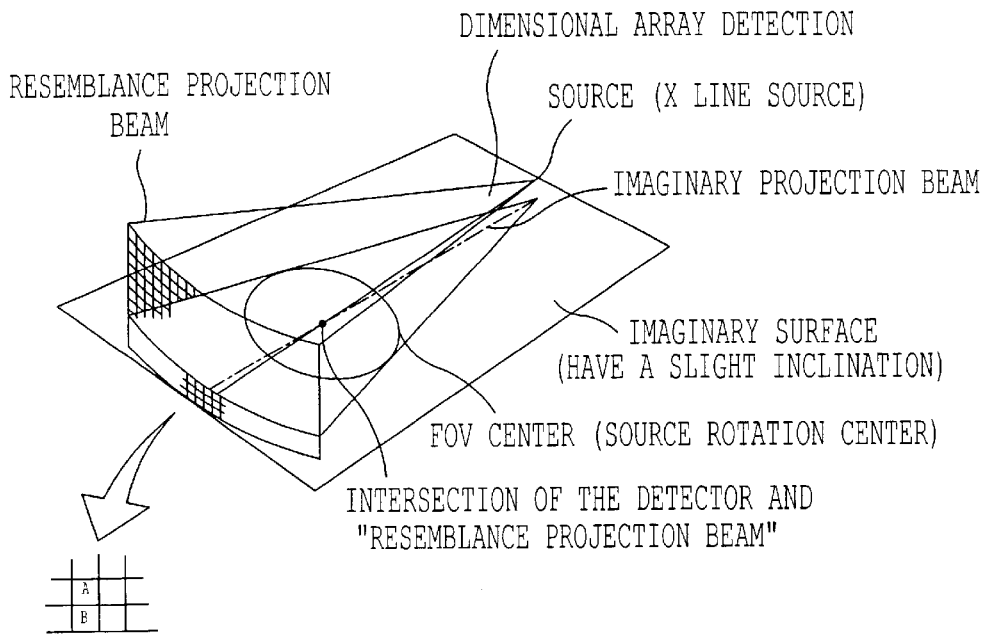
FIG. 20 is a diagram illustrating a virtual path and an approximate path at a fan interior angle of zero degrees.

Three-dimensional volume data can be acquired by repeating reconstruction processes while the slanting tomographic plane is being shifted little along the helical trajectory of the X-ray source 10. In accordance with the moving pitches of the slanting tomographic plane, spatial resolution is changed. For example, FIG. 17 shows changes of the slanting tomographic plane shifted at every angle of 90 degrees. According to this method, an image several times as much as that of a single slice or dual slice helical CT having been in practical use so far can be reconstructed by one rotation, for instance (it is varied in accordance with moving pitches).

Hereafter, the details will be described.

First, setting of virtual plane (slanting tomographic plane) to be reconstructed will be described. It has been described that the group of X-ray paths moved while the X-ray source 10 is rotated around an angle of 180 degrees approximately defines the slanting tomographic plane. However, the most approximate virtual plane having the minimum shift needs to be specified. FIG. 19 represents the helical trajectory of the X-ray source 10 (source) where the horizontal axis is the rotation angle of the X-ray source 10 and the vertical axis is the Z-coordinate. The helical trajectory of the X-ray source 10 is illustrated by a linear line f source passing through the origin. On the other hand the virtual plane is illustrated by a sine curve f plane on this graph. Here, 180°+fan angle 2A about 0°, i.e. ±(90°+A) is given as a view necessary for half scanning reconstruction. It can be easily understood that the shift between the virtual plane and the curved plane drawn by the group of X-ray paths for a half rotation of the helical trajectory of the X-ray source 10 is small as the integral of the difference between f source and f plane is small.

For example, supposing the fan angle 2A=50°, it becomes 90°+A=115°, and when the ratio of the tilt angle of the virtual plane (on the graph, it is equivalent to the inclination at an angle of zero degree in the sine curve f plane) and the inclination of f source corresponding to the relative moving rate of the bed 2 with respect to the rotation of the X-ray source 10 during helical scan is 1.095, d1 and d2, which are the differences of both functions, are nearly matched. More specifically, the virtual plane is set so as to minimize the maximum value of the absolute value of the difference between both functions (|d1–d2|), whereby the optimal virtual plane with fewest artifacts can be specified. Other than such a method according to the maximum value of the absolute value of the difference between both functions, a method may be adopted in which the virtual plane is set so as to minimize the mean square of the differences of both functions. Of course, the invention is not limited to such two methods.

Next, setting of approximate path will be discussed. As is understood with reference to FIG. 19, the virtual paths contained in the virtual plane are rare, and thus the virtual projection data rarely exists as actual projection data. Accordingly, in the fan-like X-ray beam having a certain thickness, the approximate path closest to the virtual path is set. Here, considering a fan interior angle of zero degree, the path passing through the center of FOV (Field of View) (it is the same as the rotational center of the X-ray source 10) on the virtual plane is the virtual path. On the other hand, the approximate path is given as the path passing through the center of FOV from the X-ray source 10. The actual projection data passing through the approximate path is considered to be approximate projection data regarding the fan interior angle of zero degree.

When the actual projection data passing through the approximate path does not exist, approximate projection data is generated from two sets of actual projection data of channels A and B closest to the intersection point of the approximate path and the detector plane by interpolation.

FIG. 18 conceptually illustrates changes in a group of the intersection points of the approximate path on the detector plane with respect to changes in the rotation angle by thick lines. Two kinds of specific examples are provided regarding the method for setting the approximate path.

Figure 22A:
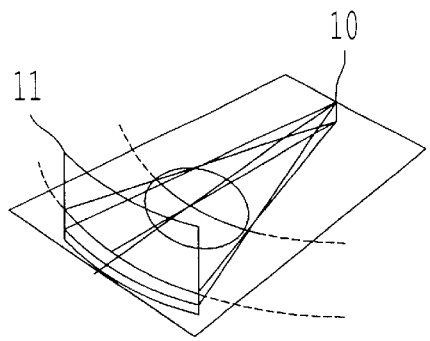
FIGS. 22a and 22b are explanatory diagrams of a method for setting an approximate path.

(1) A First Method for Setting the Approximate Path (see FIG. 22a)

In this method, observing a certain rotation angle of the X-ray source 10, the intersection points of the approximate path on the detection plane are to be drawn in a "linear line" in accordance with the changes in the fan interior angle. As described above, the approximate path at a fan interior angle of zero degree is set to cross the virtual plane at the center of FOV. The group of approximate paths is set in the manner that the intersection points of the approximate path in the other fan interior angles and the virtual plane draw a slightly flat ellipse on the virtual plane where the X-ray source 10 is taken as the center and the distance from the X-ray source 10 to the center of FOV is taken as the radius. The advantage of this method is in that the complexity is small in actual calculations.

Figure 23:
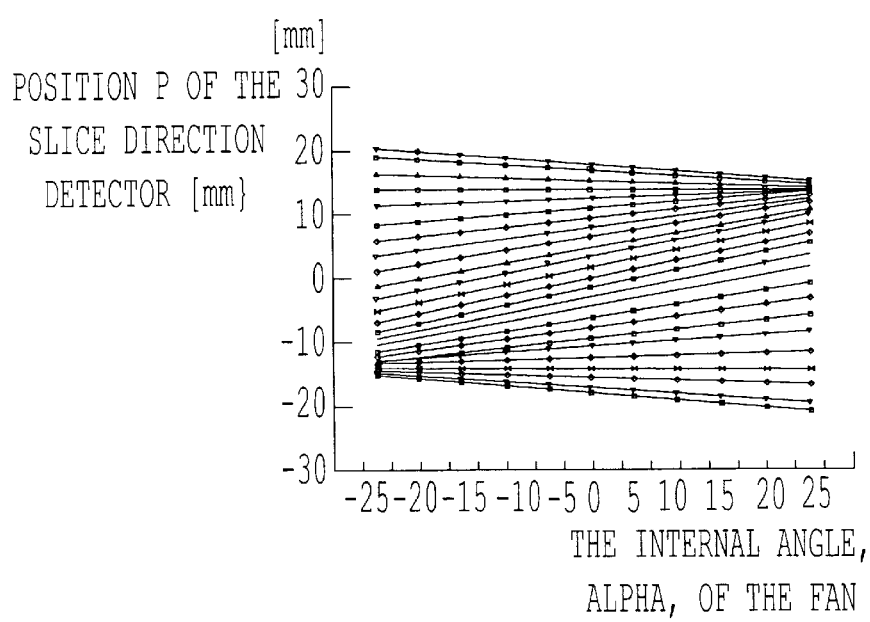
FIG. 23 is a diagram illustrating the Z-position of the entire approximate paths required for reconstructing a single tomogram.

FIG. 23 shows the entire approximate paths required for reconstructing a single tomogram according to this method. In addition, in FIG. 23, the rotation angle $\zeta$ of the X-ray source 10 is not the absolute angle; the center of a half rotation of the X-ray source 10 used for reconstruction is expressed as zero degree. The Z-position p is expressed by distance (mm) from the origin, the origin is set to the center position in the moving range where the bed 2 is moved while the X-ray source 10 is rotated a half rotation. FIG. 23 is illustrated as generalized with respect to changes in the rotation angle of the X-ray source 10 and the movement of the Z-position of the detector. FIG. 23 is illustrated such that the bed 2 is moved 40 mm in distance while the X-ray source 10 is rotated a half rotation. The way to see FIG. 23 is for example that the approximate path where the rotation angle $\zeta$ of the X-ray source 10 is zero degree and the fan interior angle $\alpha$ is zero degree is projection data where the Z-position $\rho$ is zero; it will usually exist. Of course, where the actual path for the Z-position $\rho$ does not actually exist, the approximate projection data is generated from actual projection data on two paths closest to the approximate path by interpolation.

Figure 22B:
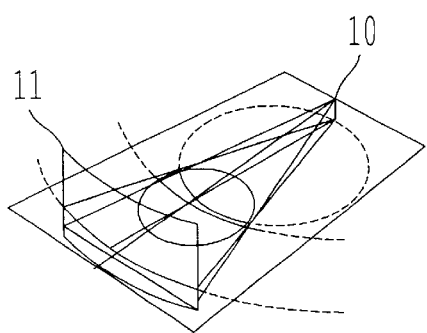

(2) A Second Method for Setting the Approximate Path (see FIG. 22b)

In this method, the approximate path is set so as to cross the virtual plane at the center of the approximate path. Such an intersection point of the approximate path and the virtual plane draws a slight ellipse where a cylinder that the circle on the XY plane is extended in the Z-axis direction crosses the slanting tomographic plane which is the virtual plane, the circle having the diameter of the distance from the X-ray source 10 to the center of FOV. Of course, when the actual projection data for the approximate path does not exist, it is generated by interpolation as described above.

As set forth, two examples of setting of the approximate path, in other words, generating approximate projection data have been described, but other modified examples can be considered, and the invention is not limited to the two examples described here. In addition, regarding interpolation, determination of interpolation coefficients beforehand for every combination of the rotation angle and the fan interior angle eliminates the calculation process of the interpolation coefficients in generating approximate projection data; it can be said that it is efficient from viewpoint of reducing calculations. Furthermore, setting of the virtual plane and the manner to take the approximate path can also be all included in the interpolation coefficients in the practical use.

Next, specific examples will be exemplified for explanation. Here, it is supposed that the rotation radius of the X-ray source 10 is set to 600 mm, the distance from the X-ray source 10 to the two-dimensional arrayed detector 11 is set to 1.1 m, and the fan angle is set to 50 degrees. At this time, FOV (a reconstructed area) is 600×sin(50°/2); it is about 250 mm. In addition, the two-dimensional arrayed detector 11 is supposed to have nine channels in the Z-direction (slice direction), that is, one-dimensional arrayed detectors are arranged in nine rows in the Z-direction. Furthermore, the one-dimensional arrayed detectors are supposed to be arranged at a row pitch equivalent to a distance of 1.4 mm at the center of FOV (at this time, the row pitch is 2.57 mm). Moreover, the distance where the bed 2 is moved while the X-ray source 10 is rotated a rotation is supposed to be 15 mm. The shift in the Z-direction of the approximate path to the virtual plane in FOV in this case can be estimated to be about 0.41 mm in both the plus and minus directions, by calculation. Projection data is extracted from the storage part 312 in accordance with FIG. 23.

The interpolation process may be any interpolation such as linear distance interpolation and interpolation using risen cosine functions. The required range of data on the two-dimensional arrayed detector 11 can be estimated to be ±10.18 mm, which falls within the range where the detector 11 exists, i.e., 2.57 mm×4=10.28 mm. Since the interpolation process is carried out during generation of approximate projection data, the executed slice thickness corresponding to the channel width of 1.4 mm at the center of FOV will become thicker and is about 2 mm. The previous error of 0.41 mm in the Z-direction is an appropriate small error; it is understood not to generate a great artifact in picture quality.

Next, image reconstruction will be described. When two-dimensional half scanning image reconstruction is performed from approximate projection data, images can be acquired. In actual processes, it is enough that the approximate projection data thus obtained undergoes only two-dimensional half scanning reconstruction in the traditional manner. At this time, when data for 180 degrees+fan angle is used, some opposite beam is obtained, but both of them may be added and averaged, or one of them may be selected. Of course, it is also acceptable that data is acquired in the range at a little wider angle and the opposite beam is "smoothly weighed and joined".

In the meantime, it is enough that the coordinate system of reconstruction is reconstructed for the X- and Y-axes orthogonal to the Z-direction, whereby the reconstruction plane has a slight inclination, but it can be acquired as an image seen from the Z-direction. The two-dimensional coordinates in the virtual plane need not be taken again. Because the original data has been collected at the X- and Y-coordinates and the continuous reconstruction planes are not in parallel as described above, it is considered that the original data at the X- and Y-coordinates are handled rather easily as three-dimensional data.

In the above description, acquisition of a single slice has been described mainly. To acquire volume data, it is enough that the range for a half rotation required for reconstructing a single image is slightly shifted (see FIG. 15a). For example, when eight images are needed during one rotation of the X-ray source 10, it is acceptable that the range for a half rotation is shifted at a pitch of 360 degrees/8=45 degrees for setting the virtual plane.

Then, even though images have been sequentially generated at a pitch of an angle of 45 degrees, for example, along the helical trajectory of the X-ray source 10, the images acquired are not in parallel. On this account, the spatial resolution is varied in the XY direction, but it is considered to reflect the spatial asymmetry of the original helical trajectory of the X-ray source 10; it can be said that it is natural in that sense.

Since the sequential images acquired are not in parallel, arbitral two-dimensional images, such as sections in parallel with each other and images of section conversion including images of curved section conversion, need to be cut out. Since each plane is given the position by Equation P ($\zeta$) described later, the plane can be calculated in accordance with the equation. In addition, when three-dimensional image processing such as surface display and projected image generation is performed, it is most convenient in operation that sections in parallel each other are once generated and then they are used for processing. However, when accuracy needs to be enhanced, it is preferred that processing is directly performed from the acquired sequential images not in parallel.

The helical CT and the dual-slice helical CT for multislice of two slices will be compared regarding the traditional method. First, the efficiency of speed and collection time for image pick-up will be described. In the previous example, when the area having a 10-cm thickness, for example, is needed as data for 2-mm slices in the helical CT, the bed was moved for 2 mm by one rotation and 50 rotations of image pick-up are needed. In the dual slice CT, the bed is moved at a distance of 4 mm by one rotation and 25 rotations of image pick-up are needed. When this method is used, the bed is moved at a distance of 15 mm by one rotation in the exemplary specific calculations, whereby image pick-up is to be done by about seven rotations.

Next, an error of the existing position of the projected beam in FOV during reconstruction will be considered. This method is an approximate technique; errors exist but it is allowed to have sufficient accuracy under appropriate conditions as the example shown in the exemplary specific calculations. Also in the traditional helical CT, the interpolation process to the adjacent data is performed; it can be said that this method can be used for execution with errors as similar to those of the traditional method.

Figure 21:
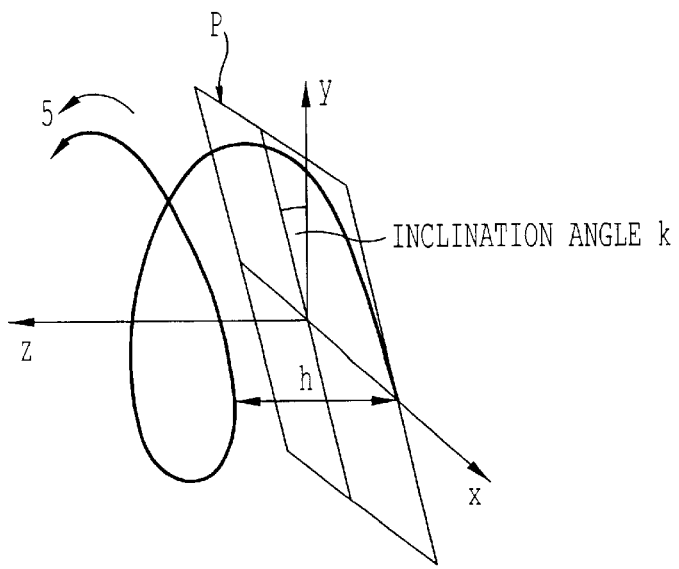
FIG. 21 is a diagram illustrating a slanting tomographic plane.
Figure 24:
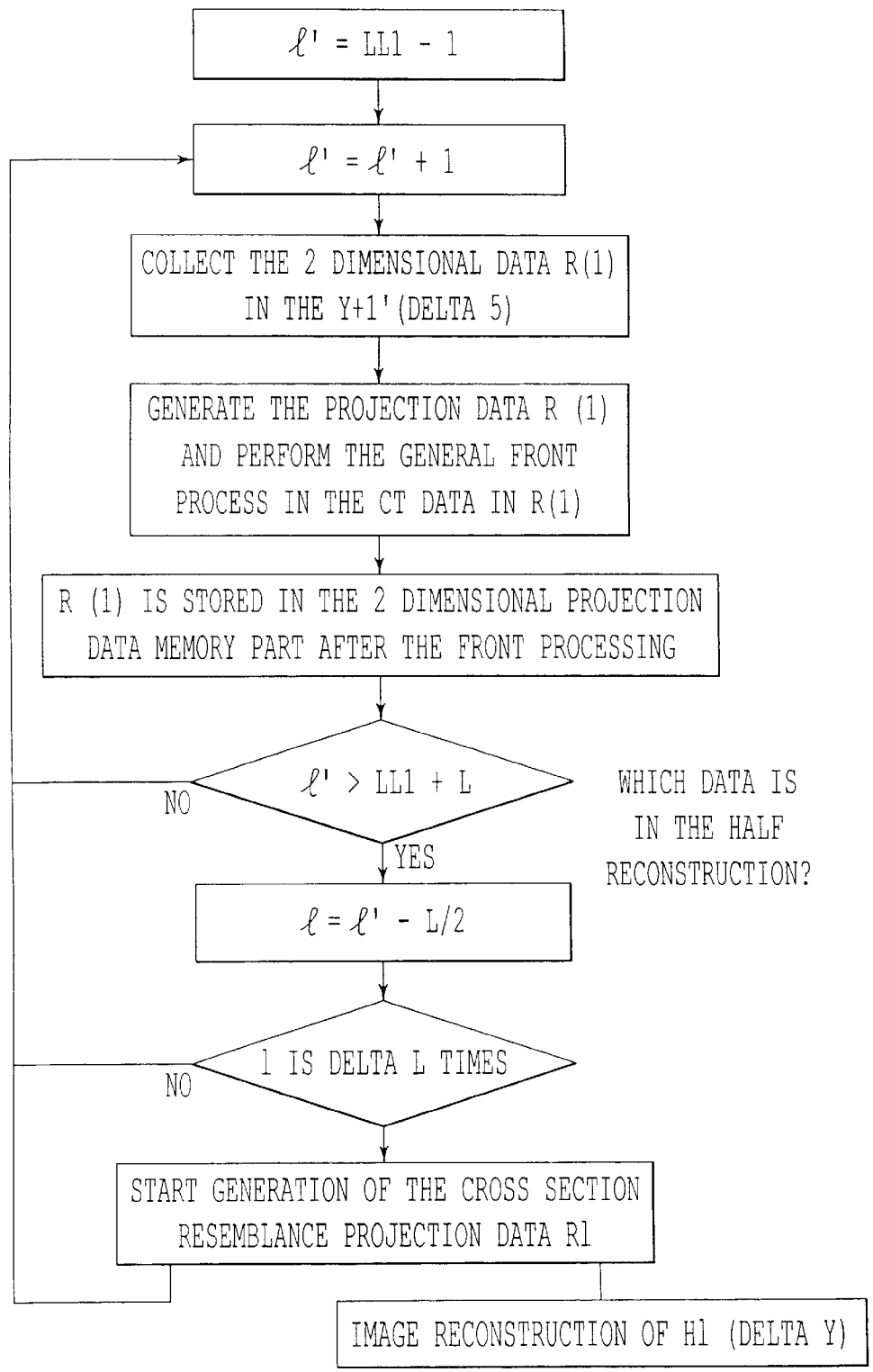
FIG. 24 is a flow diagram illustrating a flow of sequential processes from data collection to reconstruction.

FIG. 24 is a flowchart illustrating a sequential process from data collection to reconstruction. FIG. 21 shows a certain slanting tomographic plane. Supposing the distance of the bed by one rotation is set to h (mm) and the inclination of the virtual plane is set to $\kappa$, slanting tomographic plane P($\zeta$) centering the position after a $\zeta$ radian rotation, i.e. the position of ($\zeta h/2\pi$) (mm) is given by P($\zeta$)={(x,y,z) z=($\zeta h/2\pi$)+((x,y) (–sin $\zeta$, cos $\zeta$))×tan $\kappa$}, where "·" expresses an inner product.

Here, supposing the rotation angle of the X-ray source 10 is set to $\beta$, the fan interior angle is set to $\alpha$, and the position in the Z-direction is set to $\rho$, the approximate projection data for these is to be expressed by R($\beta,\alpha,\rho$). Actually, projection data is acquired discretely, and thus it is expressed by R(l($\Delta\alpha$), n($\Delta\rho$)), where m=–M/2 to +M/2, and n=–N/2 to +L/2.

Since the X-ray source 10 is rotated around several rotations by helical scan, $\beta$ has a wide range. This range I is set to I=LL1 to LL2. In addition, the range corresponding to –($\pi$/2+A) to ($\pi$/2+A) in an actual angle to be the range necessary for half scanning reconstruction is addressed by –L/2 to +L/2.

Then, the reconstruction of the slanting tomographic plane at the position where the X-ray source 10 is rotated only by $\zeta$ is considered. The Z-position $\rho$ of the approximate path on the detector for the entire approximate projection data required for reconstructing the reconstructed image H ($\zeta$) of the slanting tomographic plane is given as $\rho(\beta,\alpha)$ as the function of $\beta$ and $\alpha$.

H($\zeta$) is acquired as follows.

(STEP 1) The approximate projection data RC($\zeta,\beta,\alpha$) of the slanting tomographic plane is generated by R($\zeta,\beta,\alpha$)=R ($\zeta+\beta,\alpha,\rho(\beta,\alpha)$). At this time supposing $\zeta+\beta=(l(\zeta))\cdot(\Delta\zeta)$ $\alpha=(m(\zeta))\cdot(\Delta\alpha)$ $(n-1)\cdot(\Delta\rho)<\rho(\beta, \alpha)<n\cdot(\Delta\rho)$, actually, the approximate projection data is generated from two sets of actual projection data:

$R(l(\zeta)\cdot(\Delta\zeta), m(\zeta)\cdot(\Delta\alpha), \alpha, (n-1)\cdot(\Delta\rho))$ $R(l(\zeta)\cdot(\Delta\zeta), m(\zeta)\cdot(\Delta\alpha), \alpha, n\cdot(\Delta\rho))$ by the interpolation process.

(STEP 2) The approximate projection data R($\zeta,\beta,\alpha$) is used to reconstruct the image H($\zeta$) in the direction rotated by $\zeta$ by a predetermined half scanning reconstruction algorithm.

The approximate projection data R may be successively deleted as the continuous reconstruction of required images is completed in executing helical scan, or the reconstruction process may be executed after the completion of helical scan when the storage capacity of the storage part 312 is large enough.

The invention is not limited to the above-described embodiment, which can be modified and implemented variously. Hereafter, the modified examples will be described one by one.

(1) Combination of a Shift Mechanism

The invention is combined with the shift mechanism, whereby resolution can be enhanced. For example, supposing the rotation radius of the X-ray source 10 is "shifted" so as to be a distance of 400 mm, which is ⅔ of 600 mm in the above-described example. In this method, in conjunction with this, the distance of the bed by one rotation of the X-ray source 10 is also reduced to 10 mm, which is ⅔ of 15 mm, and the slice thickness is reduced to ⅔ as well. They are not necessarily interlocked, but it is most efficient to totally enhance the resolution including the slice direction.

(2) Use of a Partial Angular Reconstruction Method

The basic idea of this embodiment of the invention is that the fact that the extent of rotation of 180 degrees in the helical trajectory of the X-ray source 10 is approximately contained in a single plane is noticed and projection data close to the helical slanting tomographic plane is to be extracted and collected to perform usual two-dimensional half scanning reconstruction. When the helical trajectory is restricted to a part, the approximation is improved by that amount. As the modified example of this method, the partial angular reconstruction method is used in combination. With the use of this method, the approximation of the helical trajectory of the X-ray source 10 to the virtual plane in position is significantly improved, and thus images can be acquired even though the virtual plane has further inclination. Accordingly, "the fan angle in the slice direction" can also be increased, and the efficiency of image pick-up is further enhanced.

(3) Response to Counter-Rotation (Movement of the Bed in the Reverse Direction)

Regarding the direction of movement of the bed in the actual apparatus, the bed is likely to be used in both directions where the bed is inserted into and drawn out from the CT gantry. In addition, the direction of rotating the X-ray source 10 itself is considered to have two ways, including counter-rotation. In this case, the relative helical movement of the X-ray source 10 with respect to the object is mirror image symmetry, and thus the data processing (the generation of approximate projection data, the coordinates of back projection operations and the like) is to be all mirror image symmetry.

This embodiment provides the advantage that, in the computed tomographic imaging apparatus for collecting projection data by helical scan using the two-dimensional arrayed detector, approximate projection data for the X-ray path approximate to the position of the arbitrarily determined virtual plane is extracted from two-dimensional projection data actually collected and reconstructed images are reconstructed by using the approximate projection data. The approximate projection data for the X-ray path approximate to the position of the arbitrarily determined virtual plane is extracted from the two-dimensional projection data actually collected, and the approximate projection data is used to reconstruct reconstructed images, and therefore, the reconstructed images with few artifacts can be generated by simple processes in the helical scan CT using the two-dimensional arrayed detector.

Obviously, numerous modifications and variations of the present invention are possible in light of the above teachings. For example, the present invention may be implemented in the form of software stored on a recording medium, i.e., a computer program product. It is therefore to be understood that within the scope of the appended claims, the invention may be practiced otherwise than as specifically described herein.

What is claimed as new and desired to be secured by Letters Patent of the United States is:

1. A method of operating a computed tomography scanner, comprising:

conducting a helical scan at a maximum helical scan pitch given by $$r_H = \frac{2\pi}{\pi + 2\sin^{-1}\left(\frac{FOV}{2R}\right)}\left(1 - \frac{FOV}{2R}\right)$$

where FOV is a field of view of said scanner, R is a radial distance of a focal spot in said scanner to an isocenter of said scanner.

2. A method as recited in claim 1, comprising:
scanning using a fan angle comprising a virtual fan angle.

3. A method as recited in claim 2, comprising:
determining said virtual fan angle as one half of a sum a of difference between a range of angular positions of a source of said scanner in a scan and 180°.

4. A method as recited in claim 1, comprising:
scanning using a fan angle of $$2\sin^{-1}\left(\frac{FOV}{2R}\right).$$

5. A method as recited in claim 1, comprising:
using a weighting scheme with a virtual fan angle.

6. A method as recited in claim 5, comprising:
determining said virtual fan angle as one half of a sum a of difference between a range of angular positions of a source of said scanner in a scan and 180°.

7. A method as recited in claim 5, comprising:
using said weighting scheme with said virtual fan angle defined by $$2\sin^{-1}\left(\frac{FOV}{2R}\right).$$

8. A method of operating a computed tomography scanner, comprising:

scanning using a maximum helical scan pitch at a fan angle of $$2\sin^{-1}\left(\frac{FOV}{2R}\right)$$

where FOV is a field of view of said scanner and R is a radial distance of a focal spot in said scanner to an isocenter of said scanner.

9. A method as recited in claim 8, comprising:
scanning using said fan angle comprising a virtual fan angle.

10. A method as recited in claim 9, comprising:
determining said virtual fan angle as one half of a sum a of difference between a range of angular positions of a source of said scanner in a scan and 180°.

11. A method as recited in claim 8, comprising:
using a weighting scheme with said fan angle.

12. A computed tomography method, comprising:
determining a virtual fan angle greater than an actual fan angle; and
determining a helical scan pitch using said virtual fan angle.

13. A method as recited in claim 1, comprising:
scanning using said virtual fan angle defined by $$2\sin^{-1}\left(\frac{FOV}{2R}\right).$$

14. A method as recited in claim 12, comprising:
determining said virtual fan angle as one half of a sum a of difference between a range of angular positions of a source of said scanner in a scan and 180°.

15. A method as recited in claim 12, comprising:
using a weighting scheme using said virtual fan angle as said fan angle.

16. A method as recited in claim 15, comprising:
using said weighting scheme with said virtual fan angle defined by $$2\sin^{-1}\left(\frac{FOV}{2R}\right).$$

17. A computed tomography method, comprising:
exposing all voxels in a slice over a same angular range of an x-ray source of a scanner to obtain projection data;
weighting said projection data using a fan angle selected as a function of a field of view of said scanner.

18. A method as recited in claim 17, comprising:
exposing said voxels using a fan angle comprising a virtual fan angle.

19. A method as recited in claim 5, comprising:
weighting said projection data with said virtual fan angle defined by $$2\sin^{-1}\left(\frac{FOV}{2R}\right).$$

20. A computed tomography system, comprising:
an x-ray source;
an x-ray detector disposed to receive x-rays emitted from said source;
a controller connected to said source and said detector adapted to control said source to expose a subject to x-rays to obtain exposure data;
a scanner field of view dependent virtual fan angle determining device connected to said controller;
a virtual fan angle weighting device connected to said controller; and
a reconstruction processor connected to said controller.

21. A system as recited in claim 20, wherein said controller comprises:
a helical pitch determining device configured to produce a helical scan at a maximum helical scan pitch given by $$r_H = \frac{2\pi}{\pi + 2\sin^{-1}\left(\frac{FOV}{2R}\right)}\left(1 - \frac{FOV}{2R}\right)$$

where FOV is a field of view of said scanner, R is a radial distance of a focal spot in said scanner to an isocenter of said scanner.

22. A computed tomography system, comprising
a data acquisition device configured to acquire projection data by continuously scanning an object:
an weighting device configured to weight the projection data by an weighting function;
a weighting function determination device configured to determine the weighting function based on a virtual fan angle, wherein the virtual fan angle is different from a real fan angle for scanning;
a weight shifting device configured to shift the weighting function based on the acquired time of the projection data;
a reconstructing device configured to reconstruct CT images from the weighted projection data.

23. A system as recited in claim 22, wherein:
a weight shifting device shifts the weighting function along a temporal axis; and
a reconstructing device reconstructs CT images at different times.

24. A computed tomography system, comprising
a helical scanning device configured to acquire projection data of an object by a helical scanning:
an extraction device configured to extract approximate projection data of an x-ray path from the projection data, wherein the x-ray path is approximate against a virtual plane;
a weighting device configured to weight the approximate projection data by a weighting function;
a weighting function determination device configured to determine the weighting function based on a virtual fan angle, wherein the virtual fan angle is different from a real fan angle for scanning;
a reconstructing device configured to reconstruct a CT image from the weighted projection data.

* * * * *